(12) United States Patent
Beight et al.

(10) Patent No.: US 6,930,123 B2
(45) Date of Patent: Aug. 16, 2005

(54) SPLA$_2$ INHIBITORS

(75) Inventors: Douglas Wade Beight, Frankfort, IN (US); Michael Dean Kinnick, Indianapolis, IN (US); Ho-Shen Lin, Indianapolis, IN (US); John Michael Morin, Brownsburg, IN (US); Michael Enrico Richett, Indianapolis, IN (US); Daniel Jon Sall, Greenwood, IN (US); Jason Scott Sawyer, Indianapolis, IN (US); Edward C R Smith, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 64 days.

(21) Appl. No.: 10/450,929

(22) PCT Filed: Dec. 6, 2001

(86) PCT No.: PCT/US01/43184

§ 371 (c)(1),
(2), (4) Date: Jun. 16, 2003

(87) PCT Pub. No.: WO02/50028

PCT Pub. Date: Jun. 27, 2002

(65) Prior Publication Data

US 2004/0059130 A1 Mar. 25, 2004

Related U.S. Application Data

(60) Provisional application No. 60/256,281, filed on Dec. 18, 2000.

(51) Int. Cl.$^7$ ..................... A61K 31/40; C07D 209/56; A61P 29/00
(52) U.S. Cl. ....................... 514/411; 548/427
(58) Field of Search ........................... 548/427; 514/411

(56) References Cited

U.S. PATENT DOCUMENTS 3,812,112 A   5/1974   Kimura et al.

FOREIGN PATENT DOCUMENTS

| WO | WO 01/05761 | 1/2001 |
| WO | WO 01/21587 | 3/2001 |

OTHER PUBLICATIONS

Voronina et al., 1991, CAS: 115:29048.*

\* cited by examiner

*Primary Examiner*—Rita Desai
*Assistant Examiner*—Robert Shiao
(74) *Attorney, Agent, or Firm*—Francis O. Ginah

(57) ABSTRACT

A novel class of benz[f]indole compounds is disclosed together with the use of such compounds for inhibiting sPLA$_2$ mediated release of fatty acids for treatment of Inflammatory Diseases such as septic shock.

13 Claims, No Drawings

SPLA₂ INHIBITORS

This is the national phase application, under 35 USC 371, for PCT/US01/43184, filed 06 Dec. 2001, which, claims the benefit, under 35 USC 119(e), U.S. provisional application 60/256,281, filed 18 Dec. 2000.

FIELD OF THE INVENTION

This invention relates to novel benz[f]indole compounds useful for Inflammatory Diseases.

BACKGROUND OF THE INVENTION

The structure and physical properties of human non-pancreatic secretory phospholipase $A_2$ (hereinafter called, "sPLA₂") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA₂ is a rate limiting enzyme in the arachidonic acid cascade which hydrolyzes membrane phospholipids. Thus, it is important to develop compounds, which inhibit sPLA₂ mediated release of fatty acids (e.g., arachidonic acid). Such compounds would be of value in the general treatment of conditions induced and/or maintained by overproduction of sPLA₂; such as sepsis or pain.

It is desirable to develop more effective compounds and treatments for sPLA₂ induced diseases.

SUMMARY OF THE INVENTION

The present invention relates to a benz[f]indole compound of formula (I), or a pharmaceutically acceptable salt, solvate or prodrug thereof:

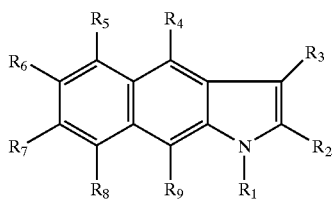

(I)

Wherein;
$R_1$ is selected from group (a), (b), or (c) wherein;
(a) is $C_2$–$C_{20}$ alkyl, $C_2$–$C_{20}$ haloalkyl, $C_2$–$C_{20}$ alkenyl, $C_2$–$C_{20}$ alkynyl, carbocyclic radical, or heterocyclic radical, or
(b) is a member of (a) substituted with one or more independently selected non-interfering substituents;
(c) is the group -(L)-$R_{80}$; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$ is hydrogen, or a group containing 1 to 10 non-hydrogen atoms plus any required hydrogen atoms;

$R_3$ is -(L₃)-Z, where -(L₃)- is a divalent linker group selected from a bond or a divalent group selected from:

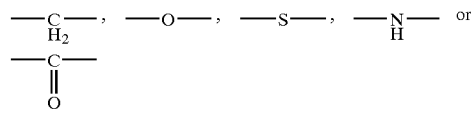

and Z is selected from an oxime amide or oxime thioamide group represented by the formulae,

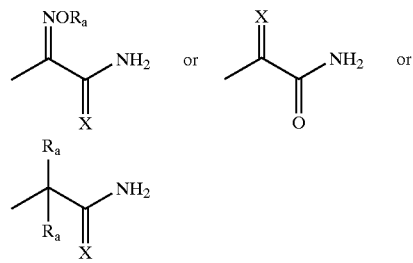

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

$R_4$ is the group, hydrogen, $CONH_2$, $CONHR^{4b}$ or -(La)-(acidic group) wherein -($L_a$)-, is an acid linker having an acid linker length of 1 to 8;

or the group -($L_h$)-(N-hydroxyfunctional amide group); wherein -($L_h$)-, is an N-hydroxyfunctional amide linker having a N-hydroxyfunctional amide linker length of 1 to 8; and wherein a N-hydroxyfunctional amide group is represented by the formula:

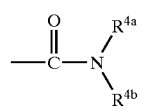

wherein $R^{4a}$ is selected from the group consisting of OH, ($C_1$–$C_6$)alkoxy, and aryloxy; and
wherein $R^{4b}$ is hydrogen or an organic substituent selected from the group consisting of ($C_1$–$C_8$)alkyl, aryl, ($C_7$–$C_{14}$) aralkyl, ($C_7$–$C_{14}$)alkaryl, ($C_3$–$C_8$)cycloalkyl, ($C_1$–$C_8$) alkoxyalkyl and these groups substituted with halogen, —$CF_3$, —OH, ($C_1$–$C_8$)alkyl, amino, carbonyl, and —CN;

or $R_4$ is the group -(Lc)- (acylamino acid group)-wherein the "acylamino acid group" is represented by the formula:

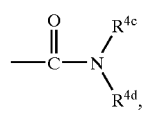

wherein $R^{4c}$ is selected from the group consisting of H, ($C_1$–$C_6$)alkyl, ($C_1$–$C_6$)alkoxy, heteroaryl and aryl, —$CF_3$; and wherein $NR^{4d}$ is an amino acid residue of either a natural or unnatural amino acid with the nitrogen atom being part of the amino group of the amino acid.

$R_5$ is selected from hydrogen, a non-interfering substituent;

$R_6$, $R_7$, $R_8$, and $R_9$ are independently selected from non-interfering substituent.

The present invention provides novel benz[f]indole compounds of formula I having potent and selective effectiveness as inhibitors of mammalian $sPLA_2$.

The present invention also relates to the use of novel benz[f]indole compounds of formula I useful in the treatment and/or prevention of Inflammatory Diseases.

This invention also relates to the use of a novel benz[f]indole compound of formula I to inhibit mammalian $sPLA_2$ mediated release of fatty acids.

The present invention provides a pharmaceutical composition containing any of the benz[f]indole compounds of the invention.

The present invention also relates to the use of a formulation comprising a compound of formula 1, and a carrier or diluent for the treatment or prevention of sepsis The present invention relates to the use of a pharmaceutical composition comprising a therapeutically effective amount of $sPLA_2$ inhibitor compounds of formula I and mixtures thereof for the manufacture of a medicament for the treatment of Inflammatory Diseases.

I. Definitions:

The terms, "mammal" and "mammalian" include human and domesticated quadrupeds.

The term, "Inflammatory Diseases" refers to diseases such as inflammatory bowel disease, sepsis, septic shock, adult respiratory distress syndrome, pancreatitis, trauma-induced shock, asthma, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enteropathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit $sPLA_2$ mediated release of fatty acid and to thereby inhibit or prevent the arachidonic acid cascade and its deleterious products.

The term, "benz[f]indole", or "benz[f]indole nucleus" as used herein refers to a nucleus (having numbered positions) with the structural formula (X):

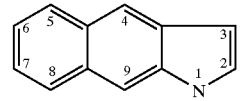

The benz[f]indole compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, sec-butyl, n-pentyl, and n-hexyl.

The term, "alkenyl" employed alone or in combination with other terms means a straight chain or branched monovalent hydrocarbon group having the stated number ranges of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo. The term, heterocyclic radical, refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, benzo(b)thiophenyl, carbazolyl, norharmanyl, azabenzo(b)thiophenyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiophenyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, benzyl, spiro[5.5]undecanyl, naphthyl, norbornanyl, bicycloheptadienyl, toluyl, xylenyl, indenyl, stilbenyl, terphenylyl, diphenylethylenyl, phenyl-cyclohexenyl, acenaphthylenyl, and anthracenyl, biphenyl, dibenzylyl and related dibenzylyl homologues represented by the formula (a):

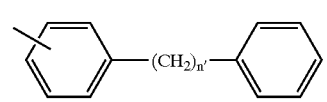

where n' is a number from 1 to 8.

The terms, "non-interfering substituent", or "non-interfering groups" refer to radicals suitable for substitution at positions 1, 2, 3, 4, 5, 6, 7, 8, and/or 9 of the benz[f]indole nucleus and on other nucleus substituents (as hereinafter described for Formula I), and radicals suitable for substitution on the heterocyclic radical and carbocyclic radical as defined above. Illustrative non-interfering radicals are ($C_1$–$C_8$)alkyl, ($C_2$–$C_8$)alkenyl, ($C_2$–$C_8$)alkynyl, ($C_7$–$C_{12}$)aralkyl, ($C_7$–$C_{12}$)alkaryl, ($C_3$–$C_8$)cycloalkyl, ($C_3$–$C_8$) cycloalkenyl, phenyl, benzyl, toluyl, xylenyl, biphenyl, ($C_1$–$C_8$)alkoxy, $C_2$–$C_8$)alkenyloxy, $C_2$–$C_8$ alkynyloxy, ($C_2$–$C_{12}$)alkoxyalkyl, ($C_2$–$C_{12}$)alkoxyalkyloxy, $C_2$–$C_{12}$ alkylcarbonyl, ($C_2$–$C_{12}$)alkylcarbonylamino, ($C_2$–$C_{12}$)alkoxyamino, ($C_2$–$C_{12}$)alkoxyaminocarbonyl, ($C_1$–$C_{12}$)alkylamino, ($C_1$–$C_6$)alkylthio, ($C_2$–$C_{12}$)alkylthiocarbonyl, ($C_1$–$C_8$)alkylsulfinyl, ($C_1$–$C_8$)alkylsulfonyl, ($C_2$–$C_8$)haloalkoxy, ($C_2$–$C_8$)haloalkylsulfonyl, ($C_2$–$C_8$)haloalkyl, ($C_2$–$C_8$)hydroxyalkyl, —C(O)O(($C_2$–$C_8$)alkyl), —(CH$_2$)$_n$—O—($C_1$–$C_8$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and carbonyl; where n is from 1 to 8 and R is ($C_1$–$C_8$)alkyl.

The term, "organic substituent" refers to a monovalent radical consisting of carbon and hydrogen with or without oxygen, nitrogen, sulfur, halogen, or other elements. Illustrative organic substituents are ($C_1$–$C_8$)alkyl, aryl, ($C_7$–$C_{14}$)aralkyl, ($C_7$–$C_{14}$)alkaryl, ($C_3$–$C_8$)cycloalkyl, ($C_1$–$C_8$)alkoxyalkyl and these groups substituted with halogen, —CF$_3$, —OH, ($C_2$–$C_8$)alkyl, amino, carbonyl, and —CN.

The term "substituted group" is an organic group substituted with one or more non-interfering substituents.

As used herein the terms "group", "radical" or "fragment" are synonymous and are intended to indicate functional groups or fragments of molecules attachable to a bond or other fragments of molecules. For example acetamide group represent the acetamide fragment or radical. Structures of groups, radicals or fragments unattached to the benz[f] indole nucleus have been drawn to show the first line as a connecting bond only. Thus, the group

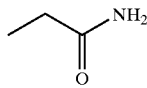

represents the acetamide radical or group, not the propanamide radical unless otherwise indicated.

The term, "N-hydroxyfunctional amide group" is represented by the formula:

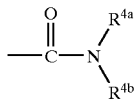

wherein $R^{4a}$ is selected from the group consisting of OH, ($C_1$–$C_6$)alkoxy, and aryloxy; and wherein $R^{4b}$ is hydrogen or an organic substituent selected from the group consisting of ($C_1$–$C_8$)alkyl, aryl, ($C_7$–$C_{14}$)aralkyl, ($C_7$–$C_{14}$)alkaryl, ($C_3$–$C_8$)cycloalkyl, ($C_3$–$C_8$)alkoxyalkyl and these groups substituted with halogen, —CF$_3$, —OH, ($C_1$–$C_8$)alkyl, amino, carbonyl, and —CN.

The phrase, "N-hydroxyfunctional amide linker" refers to a divalent linking group symbolized as, -(L$_h$)-, which has the function of joining the 4-position of the benz[f]indole nucleus to an N-hydroxyfunctional amide group in the general relationship:

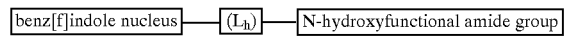

The words, "hydroxyfunctional amide linker length", refer to the number of atoms (excluding hydrogen) in the shortest chain of the linking group -(L$_h$)- that connects the 4-position of the benz[f]indole nucleus with the N-hydroxyfunctional amide group. The presence of a carbocyclic ring in -(L$_h$)- counts as the number of atoms approximately equivalent to the calculated diameter of the carbocyclic ring. Thus, a benzene or cyclohexane ring in the acid linker counts as 2 atoms in calculating the length of -(L$_h$)-. Illustrative "N-hydroxyfunctional amide linker" groups are;

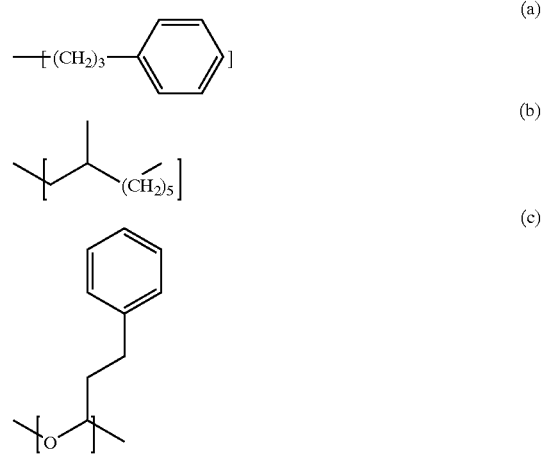

wherein, groups (a), (b) and (c) have acid linker lengths of 5, 7, and 2, respectively.

The term, "(acidic group)" means an organic group which when attached to a benz[f]indole nucleus at the 4-position, through suitable linking atoms (hereinafter defined as the "acid linker"), acts as a proton donor capable of hydrogen bonding. Illustrative of an (acidic group) are the following:

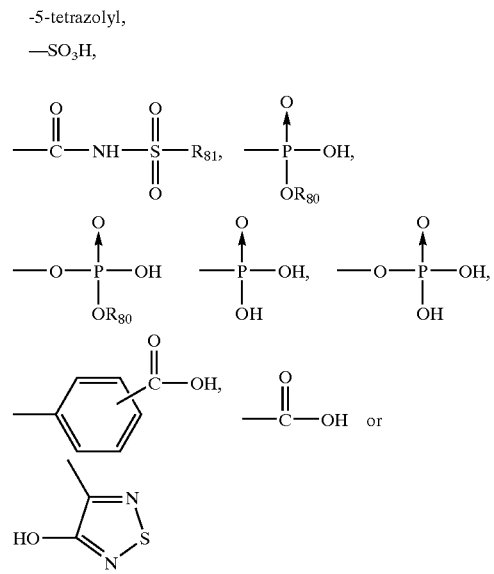

where n is 1 to 8, $R_{80}$ is a metal or ($C_1$–$C_8$) and $R_{81}$ is an organic substituent or —CF$_3$.

The words, "acid linker" refer to a divalent linking group symbolized as, -(L$_a$)-, which has the function of joining the 4-position of the benz[f]indole nucleus to an acidic group in the general relationship:

The words, "acid linker length", refer to the number of atoms (excluding hydrogen) in the shortest chain of the linking group -(L$_a$)- that connects the 4-position of the benz[f]indole nucleus with the acidic group. The presence of a carbocyclic ring in -(L$_a$)- counts as the number of atoms approximately equivalent to the calculated diameter of the carbocyclic ring. Thus, a benzene or cyclohexane ring in the acid linker counts as 2 atoms in calculating the length of -(L$_a$)-.

Illustrative acid linker groups include;

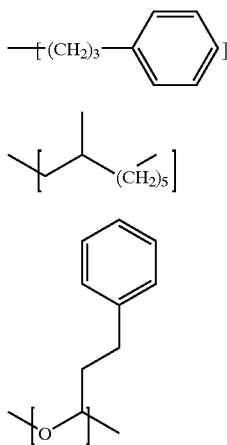

wherein, groups (a), (b), and (c) have acid linker lengths of 5, 7, and 2, respectively.

The term, "acylamino acid group" is represented by the formula:

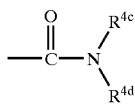

wherein R$^{4c}$ is selected from the group consisting of H, (C$_1$-C$_6$)alkyl, (C$_1$-C$_6$)alkoxy, heteroaryl and aryl, —CF$_3$; and wherein NR$^{4d}$ is an amino acid residue of either a natural or unnatural amino acid with the nitrogen atom being part of the amino group of the amino acid. A typical amino acid is selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof. Contemplated within the definition of amino acid are l-proline, d-proline and derivatives thereof. Also contemplated within the definition of amino acids are peptides, polypeptides and derivatives thereof.

The term, "amino acid residue" refers to the portion of the amino acid group coupled at the nitrogen atom of the amino terminus. It is the amino acid less a hydrogen atom from the amino terminus. It is further illustrated as used herein for the amino acid alanine attached at the nitrogen atom as shown below:

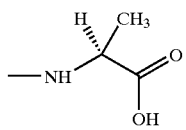

The words, "acylamino acid linker" refer to a divalent linking group symbolized as, -(L$_c$)-, which has the function of joining the 4-position of the benz[f]indole nucleus to an acylamino acid group in the general relationship:

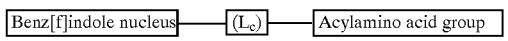

The words, "acylamino acid linker length", refer to the number of atoms (excluding hydrogen) in the shortest chain of the linking group -(L$_c$)- that connects the 4-position of the benz[f]indole nucleus with the acylamino acid group. The presence of a carbocyclic ring in -(L$_c$)- counts as the number of atoms approximately equivalent to the calculated diameter of the carbocyclic ring. Thus, a benzene or cyclohexane ring in the acid linker counts as 2 atoms in calculating the length of -(L$_c$)-. Illustrative "acylamino acid linker groups" include:

wherein, groups (a), (b) and (c) have acid linker lengths of 5, 7, and 2, respectively.

The term, "amine", includes primary, secondary and tertiary amines.

The term, "alkylene chain of 1 or 2 carbon atoms" refers to the divalent radicals, —CH$_2$—CH$_2$— and —CH$_2$—.

The term, "group containing 1 to 10 non-hydrogen atoms" refers to relatively small groups which form substituents at the 2-position of the benz[f]indole nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain no more than 4 non-hydrogen atoms such as —CF$_3$, —Cl, —Br, —NO$_2$, —CN, —SO$_3$; and (ii) groups having hydrogen atoms which contain less than 4 non-hydrogen atoms such as —CH$_3$, —C$_2$H$_5$, and —CH═CH$_2$.

The term "oxime amide" means the radical, —C(═NOR)—C(O)NH$_2$

The term "thio-oxime amide" means the radical —C(═NOR)—C(S)—NH$_2$.

The term "spiro[5.5]undecanyl" refers to the group represented by the formula;

II. The benz[f]indole Compounds of the Invention:

The present invention provides a novel class of benz[f] indole compounds useful as sPLA$_2$ inhibitors for the treatment and/or prophylaxis of inflammation attendant to inflammatory diseases. Subclasses of benz[f]indole compounds of this invention include benz[f]indole oxyacid derivatives, benz[f]indole-3-oxime amide oxyacid derivatives, benz[f]indole-3-acetamide oxyacid derivatives, benz[f]indole-3-glyoxylamide-N-hydroxyfunctional amide derivatives, benz[f]indole-3-oxime amide-N-hydroxyfunctional amide derivatives, benz[f]indole-3-acetamide hydroxy functional amide derivatives, benz[f] indole-3-glyoxylamide acylamino acid derivatives, benz[f] indole-3-oxime amide acylamino acid derivatives, benz[f] indole-3-acetamide acylamino acid derivatives.

The compounds of the invention are represented by the general formula (I) and include a pharmaceutically acceptable salt, solvate or prodrug thereof;

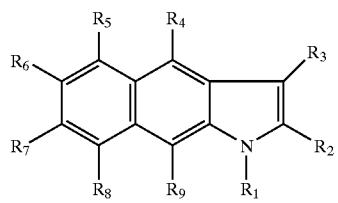 (I)

wherein;

$R_1$ is selected from group (a), (b), or (c) wherein;

(a) is $C_2$–$C_{20}$ alkyl, $C_2$–$C_{20}$ haloalkyl, $C_2$–$C_{20}$ alkenyl, $C_2$–$C_{20}$ alkynyl, carbocyclic radical, or heterocyclic radical, or (b) is a member of (a) substituted with one or more independently selected non-interfering substituents;

(c) is the group -(L)-$R_{80}$; where, -(L)- is a divalent linking group of 1 to 12 atoms selected from carbon, hydrogen, oxygen, nitrogen, and sulfur; wherein the combination of atoms in -(L)- are selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{80}$ is a group selected from (a) or (b);

$R_2$ is hydrogen, or a group containing 1 to 10 non-hydrogen atoms plus any required hydrogen atoms;

$R_3$ is -($L_3$)-Z, where -($L_3$)- is a divalent linker group selected from a bond or a divalent group selected from:

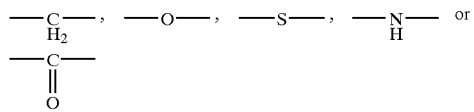

and Z is selected from an oxime amide or oxime thioamide group represented by the formulae,

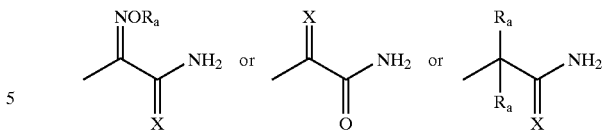

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

$R_4$ is the group, hydrogen, CONH$_2$, CONHR$^{4b}$ or -(La)- (acidic group) wherein -($L_a$)-, is an acid linker having an acid linker length of 1 to 8;

or the group -($L_h$)-(N-hydroxyfunctional amide group); wherein -($L_h$)-, is an N-hydroxyfunctional amide linker having a N-hydroxyfunctional amide linker length of 1 to 8; and wherein a N-hydroxyfunctional amide group is represented by the formula:

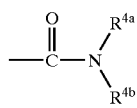

wherein $R^{4a}$ is selected from the group consisting of OH, ($C_1$–$C_6$)alkoxy, and aryloxy; and wherein $R^{4b}$ is hydrogen or an organic substituent selected from the group consisting of ($C_1$–$C_8$)alkyl, aryl, ($C_7$–$C_{14}$)aralkyl, ($C_7$–$C_{14}$)alkaryl, ($C_3$–$C_8$)cycloalkyl, ($C_1$–$C_8$)alkoxyalkyl and these groups substituted with halogen, —CF$_3$, —OH, ($C_1$–$C_8$)alkyl, amino, carbonyl, and —CN;

or $R_4$ is the group -(Lc)- (acylamino acid group)-wherein the "acylamino acid group" is represented by the formula:

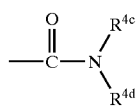

wherein $R^{4c}$ is selected from the group consisting of H, ($C_1$–$C_6$)alkyl, ($C_1$–$C_6$)alkoxy, heteroaryl and aryl, —CF$_3$; and wherein NR$^{4d}$ is an amino acid residue of either a natural or unnatural amino acid with the nitrogen atom being part of the amino group of the amino acid.

$R_5$ is selected from hydrogen, a non-interfering substituent; and $R_6$ $R_7$, $R_8$, and $R_9$ independently selected from non-interfering substituent.

Preferred Subgroups of Compounds of Formula (I):

Preferred $R_1$ Substituents:

A preferred subclass of compounds of formula (I) are those where for $R_1$ the divalent linking group -($L_1$)- is a group represented by any one of the following formulae (Ia), (Ib), (Ic), (Id), (Ie), or (If):

 (Ia)

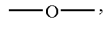 (Ib)

 (Ic)

 (Id)

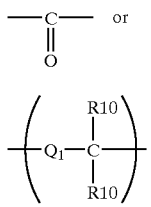

(Ie)

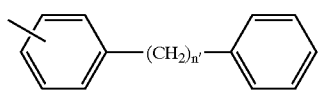

(If)

where $Q_1$ is a bond or any of the divalent groups (Ia), (Ib), (Ic), (Id), (Ie), and (If) and each $R_{10}$ is independently hydrogen, $(C_1-C_8)$alkyl, $(C_1-C_8)$haloalkyl or $(C_1-C_8)$alkoxy.

Particularly preferred as the linking group -($L_1$)- of $R_1$ is an alkylene chain of 1 or 2 carbon atoms, namely, —(CH$_2$)— or —(CH$_2$—CH$_2$)—.

The preferred group for $R_{11a}$ is a substituted or unsubstituted group selected from the group consisting of $(C_5-C_{14})$cycloalkyl, $(C_5-C_{14})$cycloalkenyl, phenyl, naphthyl, norbornanyl, bicycloheptadienyl, toluyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (a);

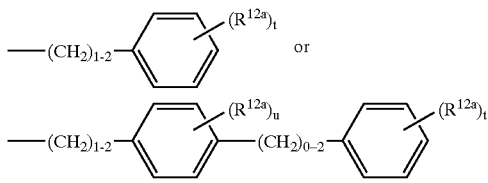

(a)

where n' is a number from 1 to 8.

Particularly preferred are compounds wherein for $R_1$ the combined group -($L_1$)-$R_{11a}$ is selected from the group consisting of

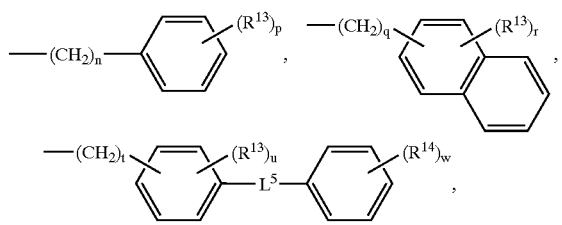

where $R^{12a}$ is a radical independently selected from halo, $(C_1-C_8)$alkyl, $(C_1-C_8)$alkoxy, —S—(($C_1-C_8$)alkyl), —O—(($C_1-C_8$)alkyl) and $(C_1-C_8)$haloalkyl where t is a number from 0 to 5 and u is a number from 0 to 4.

is the group -($L_1$)-$R_{11a}$; where, -($L_1$)- is a divalent linking group of 1 to 8 atoms and where $R_{11a}$ is a group selected from (a) or (b).

Preferred for $R_{11a}$ is —(CH$_2$)m-$R^{12a}$ wherein m is an integer from 1 to 6, and $R^{12a}$ is (d) a group represented by the formula:

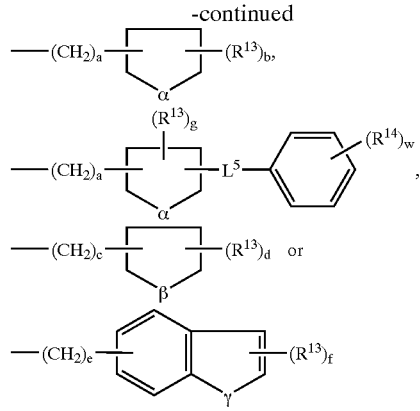

wherein a, c, e, n, q, and t are independently an integer from 0 to 2, $R^{13}$ and $R^{14}$ are independently selected from a halogen, $C_1$ to $C_8$ alkyl, $C^1$ to $C_8$ alkyloxy, $C_1$ to $C_8$ alkylthio, aryl, heteroaryl, and $C_1$ to $C_8$ haloalkyl, $\alpha$ is an oxygen atom or a sulfur atom, $L^5$ is a bond, —(CH$_2$)v-, —C=C—, —CC—, —O—, or —S—, v is an integer from 0 to 2, $\beta$ is —CH$_2$— or —(CH$_2$)$_2$—, $\gamma$ is an oxygen atom or a sulfur atom, b is an integer from 0 to 3, d is an integer from 0 to 4, f, p, and w are independently an integer from 0 to 5, r is an integer from 0 to 7, and u is an integer from 0 to 4, or is (e) a member of (d) substituted with at least one substituent selected from the group consisting of $C_1$ to $C_6$ alkyl, $C_1$ to $C_8$ alkyloxy, $C_1$ to $C_8$ haloalkyloxy, $C_1$ to $C_8$ haloalkyl, aryl, and a halogen.

Preferred $R_2$ Substituents:

$R_2$ is preferably selected from the group consisting of hydrogen, $(C_1-C_4)$alkyl, $(C_2-C_4)$alkenyl, —O—(($C_1-C_4$)alkyl), —S—(($C_1-C_3$)alkyl), —($C_3-C_4$)cycloalkyl, —CF$_3$, halo, —NO$_2$, —CN, —SO$_3$. Particularly preferred $R_2$ groups are selected from hydrogen, methyl, ethyl, propyl, isopropyl, cyclopropyl, —F, —CF$_3$, —Cl, —Br, or —O—CH$_3$.

Preferred $R_3$:

A preferred subgroups of $R_3$ is -($L_3$)-Z, where -($L_3$)- is a divalent linker group selected from a bond or a divalent group selected from:

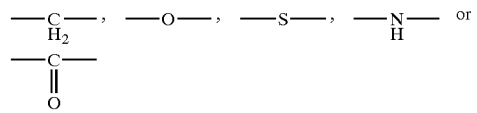

and Z is selected from a glyoxylamide, acetamide, an oxime amide or oxime thioamide group represented by the formulae,

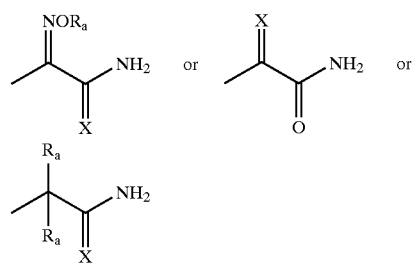

wherein X is oxygen or sulfur, $R_a$ is independently selected from hydrogen, $C_1-C_8$ alkyl, aryl, $C_1-C_8$ alkaryl, $C_1-C_8$ alkoxy, aralkyl and —CN;

A more preferred subclass of compounds of formula (I) are those wherein X is oxygen.

Also more preferred is a subclass of compounds of formula I wherein Z is a glyoxylamide (glyoxamide) group represented by

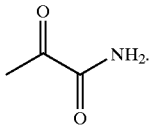

Another preferred subclass of compounds of formula (I) are those wherein Z is an amide group

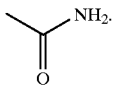

Also preferred are compounds of formula (I) wherein Z is an acetamide group represented by the formulae:

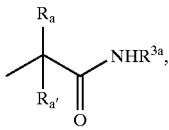

wherein $R_a$ and $R_{a'}$ are independently selected from hydrogen, $(C_1-C_8)$alkyl, aryl, $(C_1-C_8)$alkaryl, $(C_1-C_8)$ alkoxy, aralkyl and —CN, and $R^{3a}$ is hydrogen, $NH_2$, methyl, ethyl, phenyl, benzyl.

For the group $R_3$ it is most preferred that the linking group -($L_3$)- be a bond.

Preferred R4 Substituents:

A preferred subgroup of $R_4$ is the group, hydrogen, $CONH_2$, $CONHR^{4b}$ or -(La)-(acidic group) wherein -($L_a$)-, is an acid linker having an acid linker length of 1 to 8;

or the group -($L_h$)-(N-hydroxyfunctional amide group); wherein -($L_h$)-, is an N-hydroxyfunctional amide linker having a N-hydroxyfunctional amide linker length of 1 to 8; and wherein a N-hydroxyfunctional amide group is represented by the formula:

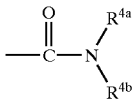

wherein $R^{4a}$ is selected from the group consisting of OH, $(C_1-C_6)$alkoxy, and aryloxy; and wherein $R^{4b}$ is hydrogen or an organic substituent selected from the group consisting of $(C_1-C_8)$alkyl, aryl, $(C_7-C_{14})$aralkyl, $(C_7-C_{14})$alkaryl, $(C_3-C_8)$cycloalkyl, $(C_1-C_8)$alkoxyalkyl and these groups substituted with halogen, —$CF_3$, —OH, $(C_1-C_8)$alkyl, amino, carbonyl, and —CN;

or $R_4$ is the group -(Lc)-(acylamino acid group)- wherein the "acylamino acid group" is represented by the formula:

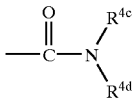

wherein $R^{4c}$ is selected from the group consisting of H, $(C_1-C_6)$alkyl, $(C_1-C_6)$alkoxy, heteroaryl and aryl, —$CF_3$;

and wherein $NR^{4d}$ is an amino acid residue of either a natural or unnatural amino acid with the nitrogen atom being part of the amino group of the amino acid. A most preferred subgroup of $R_4$ is the group, hydrogen, $CONH_2$, $CONHR^{4b}$ or -(La)-(acidic group) wherein -($L_a$)-, is an acid linker having an acid linker length of 1 to 8;

Also preferred is a subclass of compounds of formula I wherein -($L_a$)- is an acid linker selected from the group consisting of;

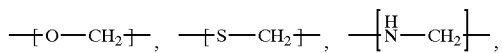

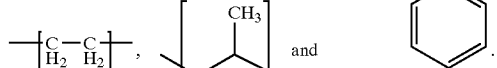

Another preferred subclass of compounds of formula I are those wherein $R_4$ is the group -(Lc)-(acylamino acid group)-, wherein -(Lc)- is an acylamino acid linker with an acylamino acid linker length of 2 or 3, and the "acylamino acid group" is represented by the formula:

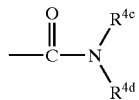

wherein $R^{4c}$ is selected from the group consisting of H, $(C_1-C_6)$alkyl, $(C_1-C_6)$alkoxy, heteroaryl and aryl, —$CF_3$; and wherein $NR^{4d}$ is an amino acid residue of either a natural or unnatural amino acid with the nitrogen atom being part of the amino group of the amino acid; and wherein the amino acid residue is derived from an amino acid selected from the group comprising isoleucine, valine, phenylalanine, aspartic acid, leucine, glycine, asparagine, cystein, glutamine, glutamic acid, histidine, lysine, methionine, serine, threonine, tryptophan, tyrosine and derivatives thereof.

Another preferred subclass of compounds of formula (I) are those wherein $R_4$ is a substituent having an N-hydroxyfunctional amide linker with an N-hydroxyfunctional amide linker length of 2 or 3 and the N-hydroxyfunctional amide linker group, -($L_h$)-, for $R_4$ is selected from a group represented by the formula;

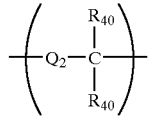

where $Q_2$ is selected from the group —$(CH_2)$—, —O—, —NH—, —C(O)—, and —S—, and each $R_{40}$ is independently selected from hydrogen, $C_1-C_8$ alkyl, aryl, $C_1-C_8$ alkaryl, $C_1-C_8$ alkoxy, aralkyl, and halo.

Most preferred subclasses of compound of formula (I) are compounds where the acid linker -(La)-, or the N-hydroxyfunctional amide linker, -($L_h$)-, or the acylamino acid linker -($L_c$)-, for $R_4$ is independently selected from the specific groups;

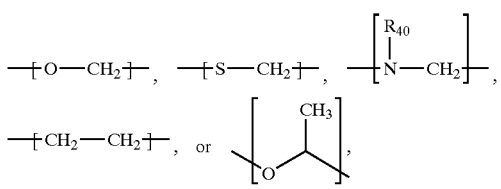

wherein $R_{40}$ is hydrogen or $(C_1-C_8)$alkyl.

Most preferred compounds of the invention are those having the general formula (II) or (III) or (IV) or a pharmaceutically acceptable salt, solvate or prodrug derivative thereof;

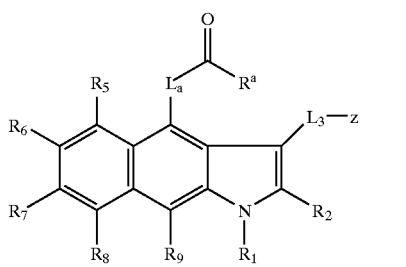

II

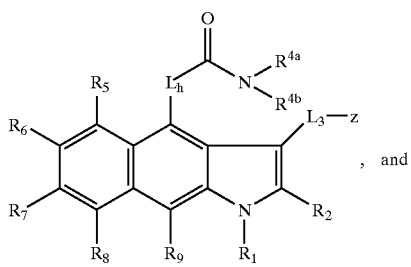

, and

III

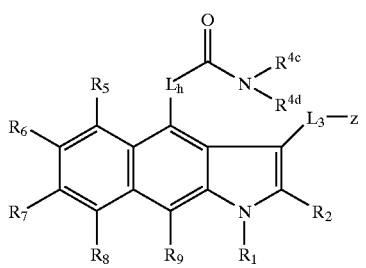

IV wherein;

$R_1$ is as described previously;

$R_2$ is as described previously;

$R_3$, $R_4$, $R_5$, $R_6$, $R_7$, $R_8$, and $R_9$ are as described previously;

$L_3$ is preferably a bond;

$L_a$, $L_h$, and $L_c$ are each preferably the group —OCH$_2$—;

and Z is selected from an amide, thioamide or glyoxylamide, acetamide or thioacetamide, oxime, hydrazide radical (group) represented by the formulae,

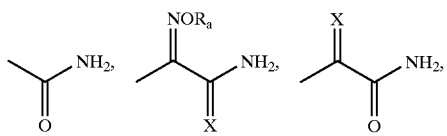

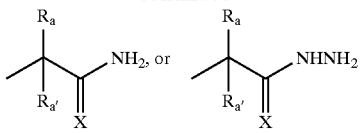

wherein X is oxygen or sulfur, $R_a$ and $R_{a'}$ are independently selected from hydrogen, $(C_1-C_8)$alkyl, aryl, and $(C_1-C_8)$alkaryl.

Preferred compounds of the invention are represented by the formulae (C1), (C2), (C3), (C4), (C5), (C6), (C7), (C8), (C9), or (C10):

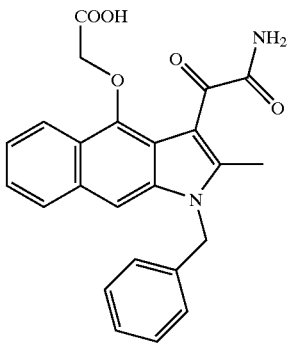

(C1)

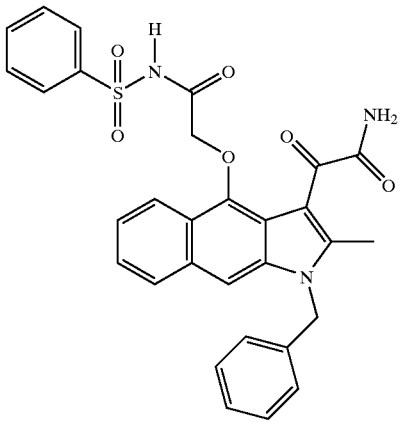

(C2)

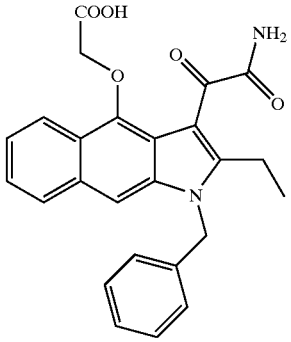

(C3)

-continued (C4) 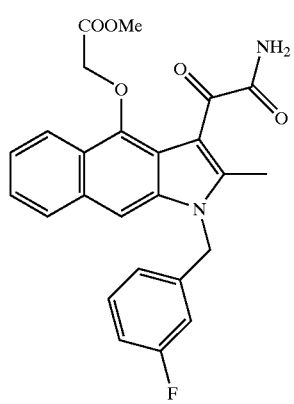

(C5) 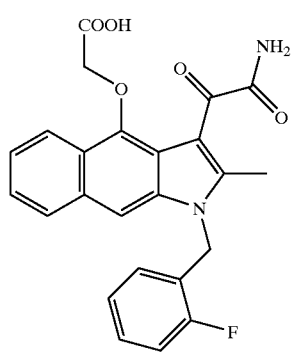

(C6) 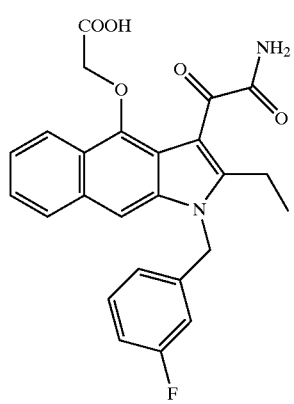

(C7) 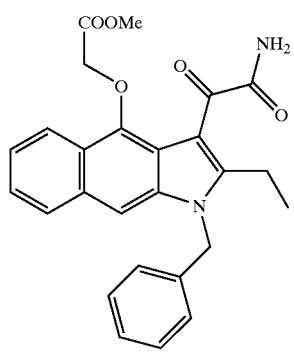

-continued (C8) 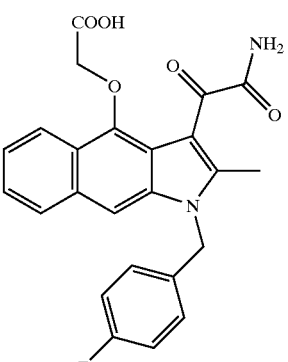

(C9) 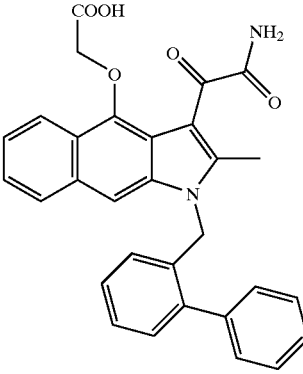

, or (C10) 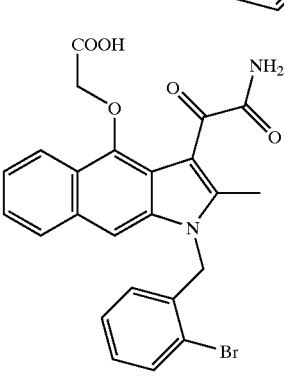

Most preferred compounds (and all pharmaceutically acceptable salts, solvates and prodrug derivatives thereof) which are illustrative of the compounds of the invention for treatment of a human afflicted with Inflammatory Disease, a pharmaceutically acceptable salt, solvate, or a prodrug derivative of a compound selected from the group consisting of:

2-[[3-(2-amino-1,2-dioxoethyl)-1-benzyl-2-ethyl-1H-benz[f]indol-4-yl]oxy]acetic acid ethyl ester;

2-[[3-(2-amino-1,2-dioxoethyl)-1-benzyl-2-ethyl-1H-benz[f]indol-4-yl]oxy]acetic acid benzyl ester; and 2-[[3-(2-amino-1,2-dioxoethyl)-1-benzyl-2-ethyl-1H-benz[f]indol-4-yl]oxy]acetic acid.

The salts of the benz[f]indole compounds represented by formulae (I), (II), (III), and (IV) are an additional aspect of the invention.

In those instances when the compound of the invention possesses acidic or basic functional groups, various salts may be formed which are more water soluble and more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of stereoisomers and diastereomers, because they have different melting points, different boiling points, and different solubilities and can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of formula (I) (in a medium such as dimethylformamide) with 4-(2-chloroethyl) morpholine hydrochloride (available from Aldrich Chemical Co., Milwaukee, Wis. USA, Item No. C4, 220-3).

(III) Method of Preparing the benz[f]indole-3-glyoxylamide Compound:

The benz[f]indole-3-glyoxylamide compounds are compounds of this invention and are also useful as intermediates or starting materials for preparing other compounds of the invention. The benz[f]indole-3-amide compounds are prepared by following a protocol such as Scheme 1 below:

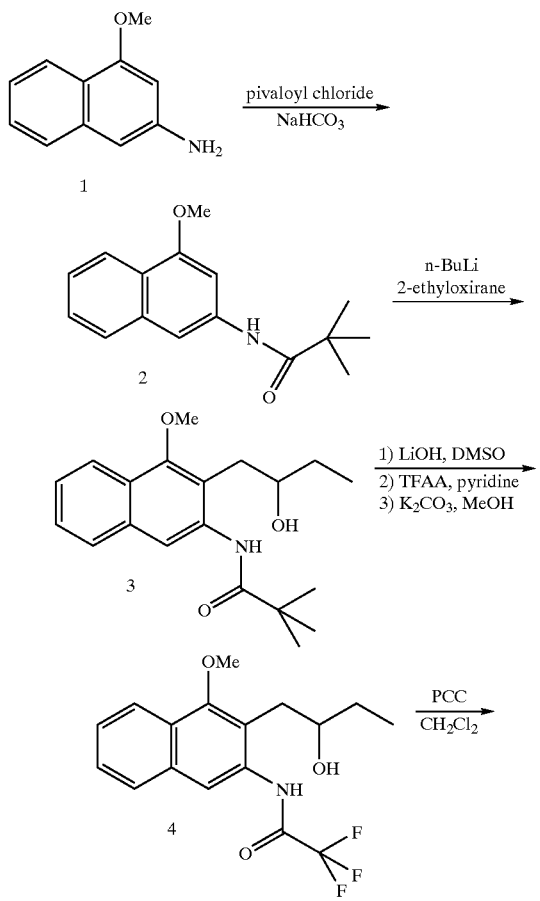

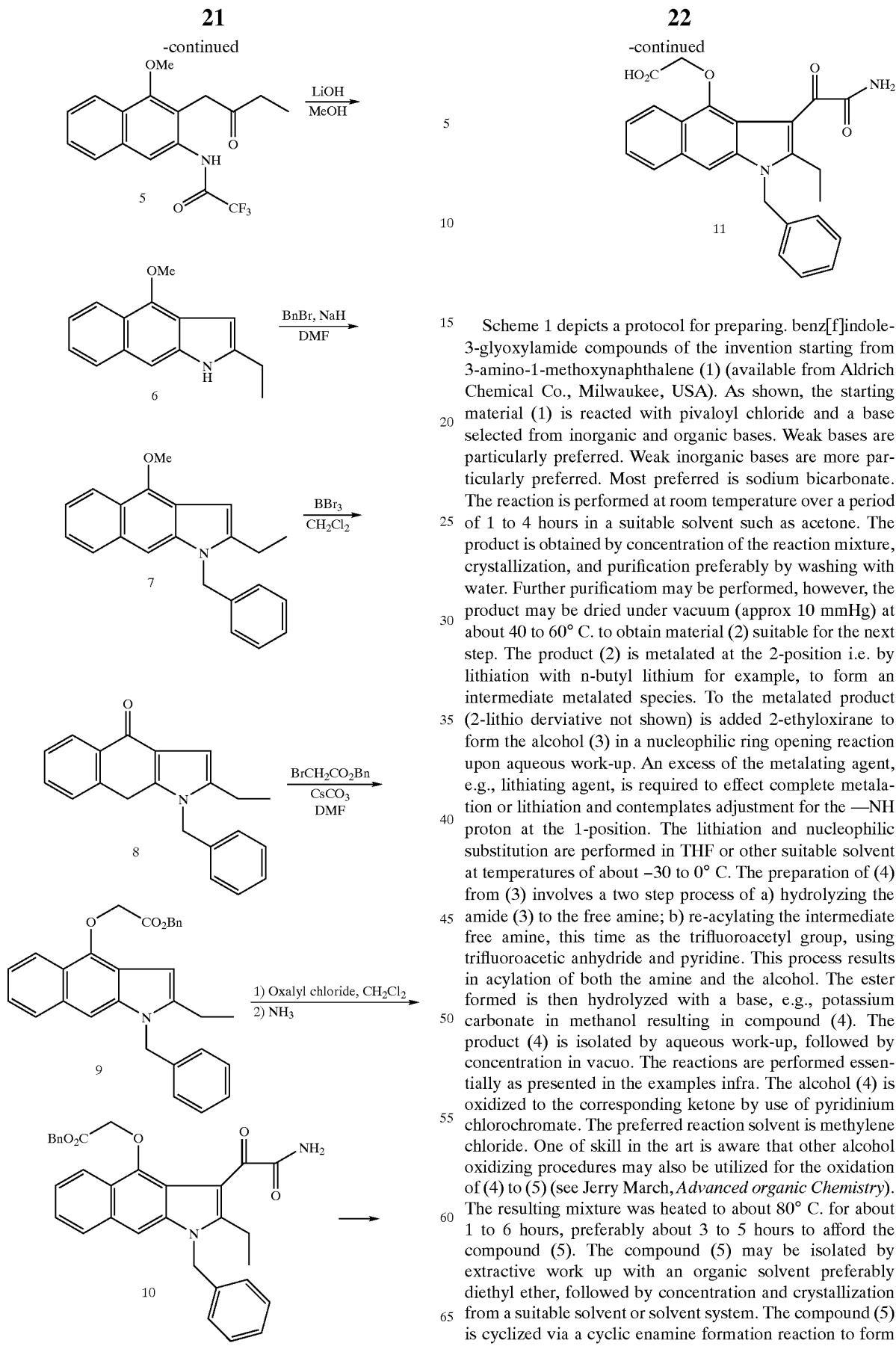

Scheme 1 depicts a protocol for preparing. benz[f]indole-3-glyoxylamide compounds of the invention starting from 3-amino-1-methoxynaphthalene (1) (available from Aldrich Chemical Co., Milwaukee, USA). As shown, the starting material (1) is reacted with pivaloyl chloride and a base selected from inorganic and organic bases. Weak bases are particularly preferred. Weak inorganic bases are more particularly preferred. Most preferred is sodium bicarbonate. The reaction is performed at room temperature over a period of 1 to 4 hours in a suitable solvent such as acetone. The product is obtained by concentration of the reaction mixture, crystallization, and purification preferably by washing with water. Further purificatiom may be performed, however, the product may be dried under vacuum (approx 10 mmHg) at about 40 to 60° C. to obtain material (2) suitable for the next step. The product (2) is metalated at the 2-position i.e. by lithiation with n-butyl lithium for example, to form an intermediate metalated species. To the metalated product (2-lithio derviative not shown) is added 2-ethyloxirane to form the alcohol (3) in a nucleophilic ring opening reaction upon aqueous work-up. An excess of the metalating agent, e.g., lithiating agent, is required to effect complete metalation or lithiation and contemplates adjustment for the —NH proton at the 1-position. The lithiation and nucleophilic substitution are performed in THF or other suitable solvent at temperatures of about −30 to 0° C. The preparation of (4) from (3) involves a two step process of a) hydrolyzing the amide (3) to the free amine; b) re-acylating the intermediate free amine, this time as the trifluoroacetyl group, using trifluoroacetic anhydride and pyridine. This process results in acylation of both the amine and the alcohol. The ester formed is then hydrolyzed with a base, e.g., potassium carbonate in methanol resulting in compound (4). The product (4) is isolated by aqueous work-up, followed by concentration in vacuo. The reactions are performed essentially as presented in the examples infra. The alcohol (4) is oxidized to the corresponding ketone by use of pyridinium chlorochromate. The preferred reaction solvent is methylene chloride. One of skill in the art is aware that other alcohol oxidizing procedures may also be utilized for the oxidation of (4) to (5) (see Jerry March, *Advanced organic Chemistry*). The resulting mixture was heated to about 80° C. for about 1 to 6 hours, preferably about 3 to 5 hours to afford the compound (5). The compound (5) may be isolated by extractive work up with an organic solvent preferably diethyl ether, followed by concentration and crystallization from a suitable solvent or solvent system. The compound (5) is cyclized via a cyclic enamine formation reaction to form compound (6). The is effected by using a base e.g., lithium hydroxide in methanol to possibly generate a nucleophilic nitrogen atom which attacks the carbonyl group of the ketone at the carbon atom. This results in a cyclic carbinol intermediate. The cyclic carbinol intermediate upon a subsequent abstraction of a hydrogen atom eliminates a molecule of water to form compound (6). The exact mechanism for the formation of any intermediate or product is not critical to the invention. The compound (6) is then substituted at the nitrogen by reaction with electrophilic groups to introduce the $R_1$ group. This is accomplished by a base catalyzed de-protonation followed by a nucleophilic attack on an electrophile. Electrophiles suitable for this reaction are those necessary to incorporate the $R_1$ group described previously and include for example, alkyl, cycloalkyl, aryl, and arylalkyl groups as the halides, sulfonates or other leaving groups. For example, the reaction of compound (6) with sodium hydride or a suitable base including for example, n-BuLi, lithium diisopropyl amide, and the like in a suitable sovent e.g., dimethylformamide, followed by addition of benzyl bromide for example, affords upon work-up the compound of formula (7).

The compound (7) is de-methylated by reaction with boron tribromide or sodium thioethoxide in a suitable solvent such as dichloromethane. About 1.0 to 2.0 equivalents of boron tribromide, for example, is typically sufficient to effect complete de-methylation. The de-methylation reaction temperature is from about −12° C. to about 10° C. Work-up is effected by stirring with methyl alcohol or other suitable protic solvent. The stirring in methyl alcohol is followed by neutralization with a base e.g., sodium bicarbonate. This is followed by extraction, and purification of the organic phase by methods known to one of skill in the art. The product (8) is possibly a tautomer between the keto and enol forms, however, nuclear magnetic resonance analysis shows the isolated product as the keto tautomer. The product (8) is dissolved in N,N-dimethylformamide followed by addition of a slight excess (about 1.05 mole equiv. based on (7)) of cesium carbonate or other mild base, and a substituted haloacetate, e.g., benzylbromoacetate or methylbromo acetate, to afford a compound (9). Compound (9) is obtained after about 1 to 30 hours, preferably about 1 to 6 hours of reaction at about room temperature. Compound (9) is isolated by aqueous extraction followed by chromatography.

The compound of formula (9) may be reacted with oxalyl chloride in a suitable solvent, e.g., methylene chloride at about 0 to 10° C. for about 1 hour. This is followed by reaction with ammonia (THF solution saturated with ammonia) to afford the compound of formula (10).

The free acid (11) is optionally obtained by acidifying the saponification product of (10) or other basification reaction product, e.g. with potassium or lithium hydroxide. Most strong inorganic acids are suitable for acidification as described previously. However, the use of dilute HCl is preferred. The free acid (11) may be extracted into an organic phase if soluble, and dried by common laboratory methods or dried by removing water from the aqueous phase. Alternatively the saponification reaction (sodium hydroxide reaction with (10)) product, itself a compound of the invention may be isolated.

Conversion of the 3-glyoxylamide intermediate to the acylamino acid group or the N-hydroxyfunctional amide group derivative at 4-position is shown for example in Scheme 1b below:

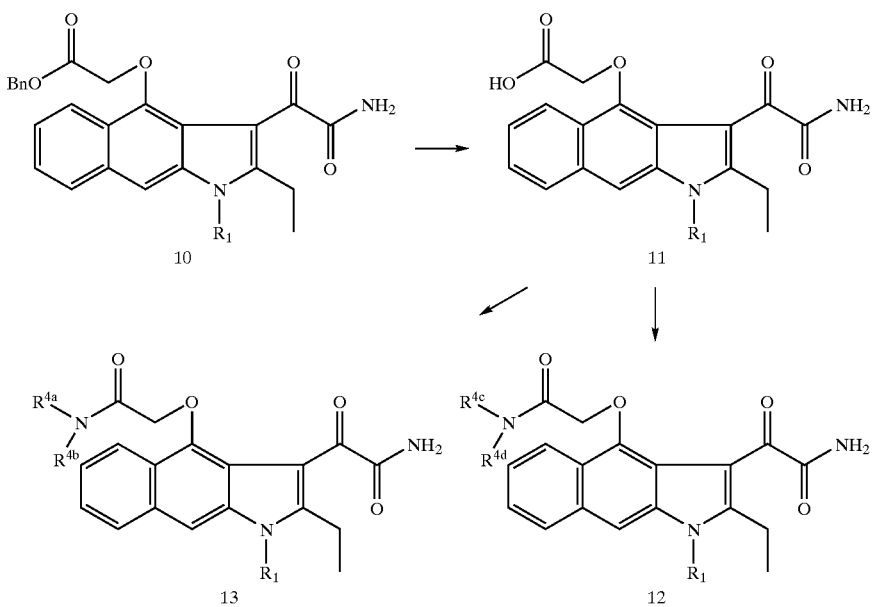

Scheme 1b

According to Scheme 1b, the oxyacetic acid ester (10) may be converted to the free acid (11) or to derivatives such as the ester or amide by procedures known to one of skill in the art or found in general reference texts. See for example, J. March *Advanced Organic Chemistry*, Wiley Interscience publishers, New York, N.Y., 1985, and R. C. Larock *Comprehensive Organic Transformations*, VCH Publishers, New York, N.Y., 1989. The acid (11) is functionalized at the 4-position to the acylamino acid derivative (12) by room temperature base catalyzed condensation with an amino acid protected at the acid terminus (using a protecting group known in the literature but preferably the methyl ester). The reaction is accomplished using coupling agents such as HOBT/EDCI, BOP/collidine or other amide bond forming coupling agents known to one of skill in the art.

The N-hydroxyfunctional amide group may be introduced via the acid (11) or acid salt-thereof, by reaction with for example hydroxylamine hydrochloride or substituted hydroxylamine hydrochloride to afford the N-hydroxyfunctional amide compound of formula (13) upon deprotection and/or aqueous work-up. For example, the acid compound (11) is reacted with o-(tert-butyldimethylsilyl) hydroxylamine at ambient temperature, in the presence of excess 2,4,6-collidine (collidine) and benzotriazol-1-yl-oxytris(dimethylamino)phosphonium hexafluorophosphonate (coupling catalyst, see *Tetrahedron Lett.*, 1219 (1975)) to afford after about 1–10 hours, the o-(tert-butyldimethylsilyl) substituted N-hydroxyfunctional amide derivative (not shown). The silyl or other protecting group is removed by well known methods such as, for example, the use of trifluoroacetic acid for removal of silyl protecting groups) to afford, for example, the N-hydroxyfunctional amide compound (13) wherein $R^{4a}$ is hydroxy and $R^{4b}$ is hydrogen.

Typically, the condensation or coupling is performed in a solvent such a dimethylformamide, tetrahydrofuran or aqueous mixtures of the like. In general protic solvents are preferred for the purpose of this invention. A base including for example, weak organic or inorganic bases catalyzes the reaction. Organic bases such as collidine are preferred. The reaction is also preferably run in the presence of agents that retard or reduce racemization of the hydroxyfunctional amide, the substituted hydroxylamine or its derivative. A particularly preferred agent is benzotriazolyl-N-oxy-tris (dimethylamino)phosphonium hexafluorophosphate. Upon completion of the reaction, the mixture is concentrated in vacuo. The resulting product mixture is chromatographed or crystallized, e.g., by sonication to obtain the target compound.

Benz[f]indol-3-acetamide sPLA$_2$ inhibitor derivatives of compounds (8) may be obtained by lithiation of compound (8) at the 3-position with an organolithium reagent e.g. n-butyllithium, followed by quenching the lithiated intermediate with ethylene oxide to afford the terminal alcohol derivative (14) upon hydrolysis. The protocol is shown below in Scheme 2.

Scheme 2

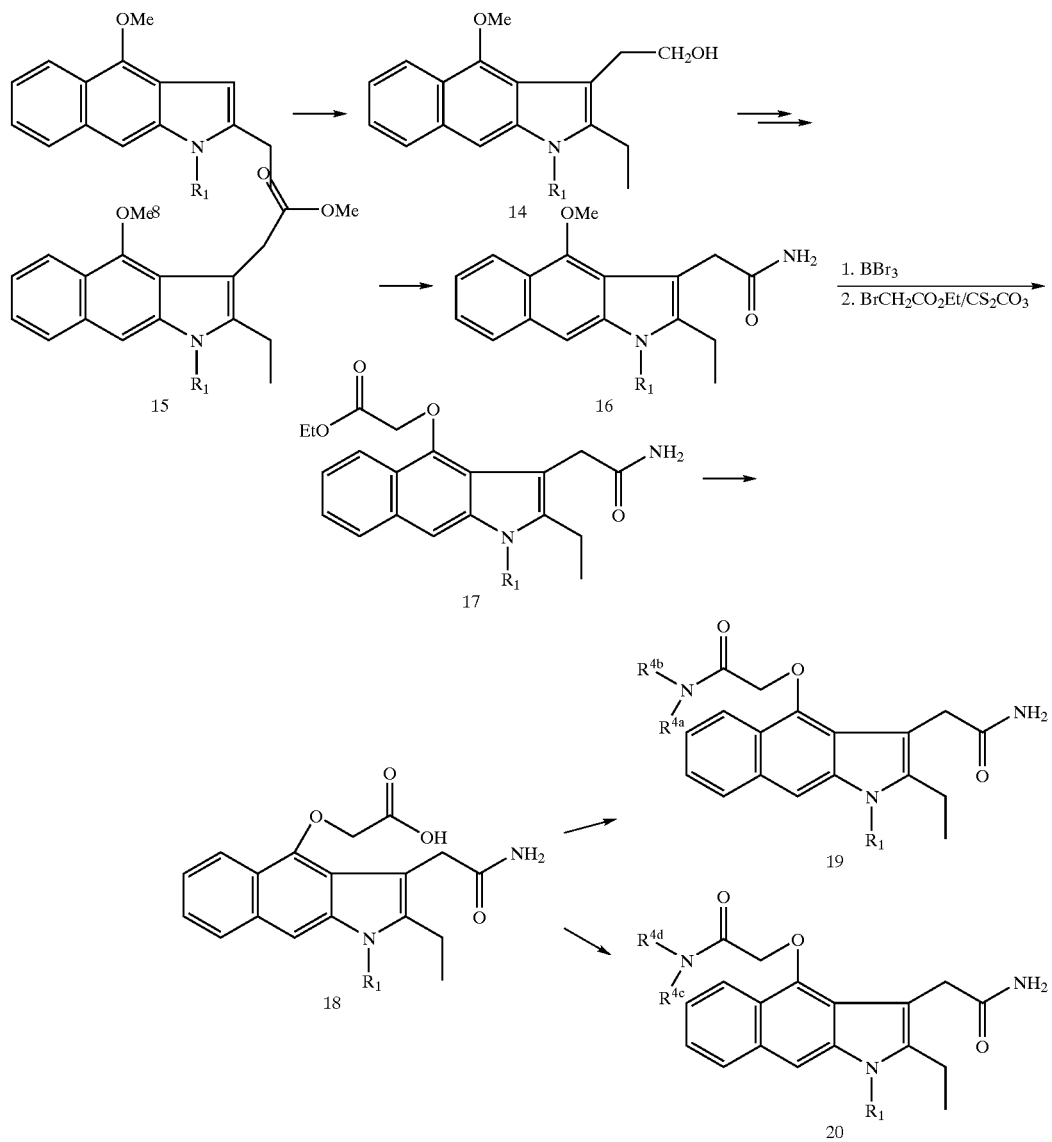

The resulting alcohol intermediate (14), itself a compound of the invention, may be converted by oxidation to the acid and further converted to the ester (15). Conversion of the alcohol intermediate (14) to an ester via an intermediate acid may be accomplished, for example, by oxidation of the alcohol with sodium hypochlorite in buffered t-butanol followed by esterification of an intermediate acid to the ester (15). The intermediate acid may be isolated if desired. Methods for these conversions are known to one of skill in the art and may be found in general reference texts disclosed herein. The ester (15) may be converted to the acetamide derivative (16) or other substituted acetamide compound. For example the reaction of the methyl acetate (15) with methylchloroaluminum amide in benzene or other suitable solvent or solvent mixtures affords the acetamide (compound 16). (See Levin, J. I. ; Turos, E.; Weinreb, S. M. *An alternative procedure for the aluminum-mediated conversion of esters to amides. Syn.Comm.,* 1982, 12, 989–993).

Similarly, use of N-substituted methylchloroaluminum amides result in the corresponding substituted acetamides (see Weinreb supra). Alternatively the terminal alcohol (15) could be converted to the acid halide (i.e., chloride) via the acid (alcohol oxidation product). The acid halide is then ammoniated to form the acetamide or substituted acetamide depending on amine used.

The 3-substituted benz[f]indole acetamide compounds described above may be converted to the corresponding 4-substituted N-hydroxyfunctional amide compounds (19) or the 4-substituted acylamino acid compounds (20) as described previously for the glyoxylamide compounds (Scheme 1b). For example, the methoxy group at the 4-position of compound (16) may be de-methylated as described above, reacted with bromomethylacetate and cesium bromide in DMF to form the oxyacetic acid ester group at the 4-position (compound 17). The oxyacetic acid ester group of (17) is further elaborated to the acid (18). The acid (18) is converted to the N-hydroxyfunctional amide group or the N-acylamino acid group as discussed above.

The substituted benz[f]indol-3-oxime amide compounds of the invention can be prepared following protocol of Scheme (3) below:

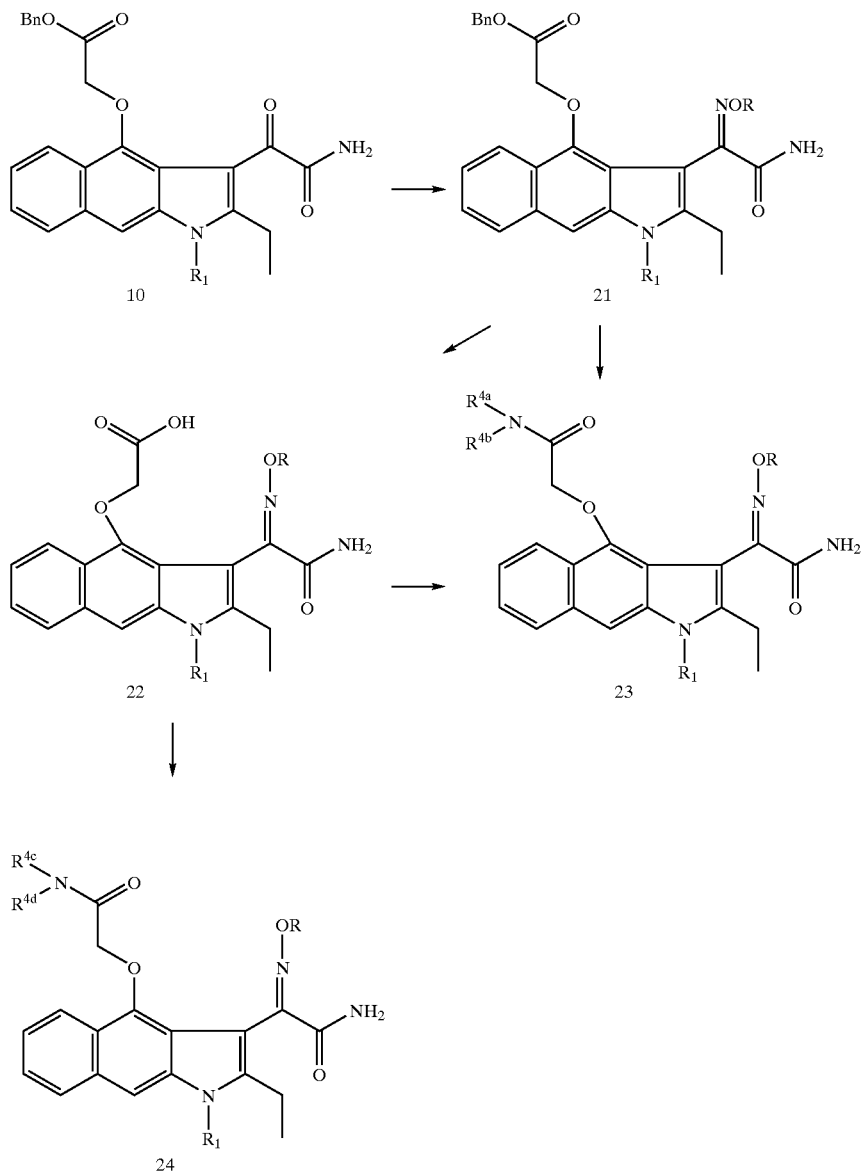

To introduce the oxime functionality, the compound of formula (10), for example, is heated with hydroxylamine hydrochloride (when R is H) in a THF/methanol mixture for about 1 to 8 hours or until the reaction is deemed satisfactorily complete. The reaction product compound (21), a compound of the invention, is isolated by chromatography or other known laboratory procedure. Substituted oximes such as when R is methyl, ethyl, phenyl or other non-interfering substituent may be prepared by reaction of the corresponding substituted hydroxylamine hydrochloride or free base with the glyoxylamide (e.g. compound (10)) as described supra.

Similarly, the ester i.e. methylester of the acid compound (11), or the acid salts thereof, may be converted to the corresponding oxime or substituted oxime functionality at the 3-position by the method described above. The ester functionality at the 4-position on the substituted benz[f]indole nucleus, as in for example, compound (21), may be converted to the acid by hydrolysis using lithium hydroxide or other known ester hydrolysis methods to afford a compound of formula (22). See, for example, J. March *Advanced Organic Chemistry*, Wiley Interscience publishers, New York, N.Y., 1985, and R. C. Larock *Comprehensive Organic Transformations*, VCH Publishers, New York, N.Y., 1989.

Furthermore, the oxime compounds prepared as described above may be converted to the N-hydroxyfunctional amide at the 4-position, via the ester (21), the free acid (22), or the acid salt functionalities at the 4-position. For example, Scheme (3) shows the conversion of the free acid compound (22) to the N-hydroxyfunctional amide compound (23).

Likewise, the compound (22) and analogs thereof may be converted to the acylamino acid compound (24) and corresponding homologs thereof, by procedures described supra.

IV. Methods of Using the Compounds of the Invention:

The benz[f]indole compounds described herein are believed to achieve their beneficial therapeutic action principally by direct inhibition of mammalian (including human) sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of fatty acids comprises contacting mammalian sPLA$_2$ with a therapeutically effective amount of benz[f]indole compounds corresponding to Formulae (I) or (II) or (III) or (IV) as described herein including a combination thereof, a salt or a prodrug derivative thereof.

Another aspect of this invention relates to a method for treating Inflammatory Diseases such as inflammatory bowel disease, septic shock, adult respiratory distress syndrome, pancreatitis, trauma, asthma, bronchial asthma, allergic rhinitis, rheumatoid arthritis, osteoarthritis, and related diseases which comprises administering to a mammal (including a human) a therapeutically effective dose of a benz[f]indole compound of the invention.

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effect will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention per Formula (I) or (II) or (III) or (IV) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the benz[f]indole compound of the invention together with a pharmaceutically acceptable carrier or diluent therefor. The present pharmaceutical formulations are prepared by known procedures using well-known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substance, which may also act as flavoring agents, lubricants, solubilizers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. A preferred tablet formulation for oral administration is one that affords rapid dissolution in the mouth of a patient in need thereof.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or (II) or (III) or (IV) or a pharmaceutically acceptable salt, solvate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of Active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of Active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of Active ingredient, are made as follows:

| Active ingredient | 225 mg |
| --- | --- |
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of Active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| Active ingredient | 100 mg |
| Isotonic saline | 1,000 ml |

The solution of the above ingredients generally is administered intravenously to a subject at a rate of 1 ml per minute.

Assay

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:

| | |
|---|---|
| REACTION BUFFER - | |
| $CaCl_2.2H_2O$ | (1.47 g/L) |
| KCl | (7.455 g/L) |
| Bovine Serum Albumin (fatty acid free) (Sigma A-7030, product of Sigma Chemical Co., St. Louis MO, U.S.A.) | (1 g/L) |
| TRIS HCl | (3.94 g/L) |
| pH 7.5 (adjust with NaOH) | |
| ENZYME BUFFER - | |
| 0.05 $NaOAc.3H_2O$, pH 4.5 | |
| 0.2 NaCl | |
| Adjust pH to 4.5 with acetic acid | |
| DTNB - 5,5'-dithiobis-2-nitrobenzoic acid | |
| RACEMIC DIHEPTANOYL THIO - PC | |
| racemic 1,2-bis(heptanoylthio)-1,2-dideoxysn-glycero-3-phosphorylcholine | |
| TRITON X-100 ™ prepare at 6.249 mg/ml in reaction buffer to equal 10 uM. | |

Reaction Mixture

A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

Tests were done in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were re-assayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ values were determined by plotting log concentration versus inhibition values in the range from 10–90% inhibition.

Results

| Compound of Example# | $IC_{50}$ ($\mu M$) (micromolar) |
|---|---|
| 1 | 1.30 |
| 2 | 14.3 |
| 3 | 1.06 |

While the present invention has been illustrated above by certain specific embodiments, it is not intended that these specific examples should limit the scope of the invention as described in the appended claims.

Experimental

All of the products of the Examples described below as well as intermediates used in the following procedures showed satisfactory NMR and IR spectra. They also had the correct mass spectral values.

EXAMPLE 1

Preparation of 2-[[3-(2-amino-1,2-dioxoethyl)-1-benzyl-2-ethyl-1H-benz[f]indol-4-yl]oxy]acetic acid ethyl ester.

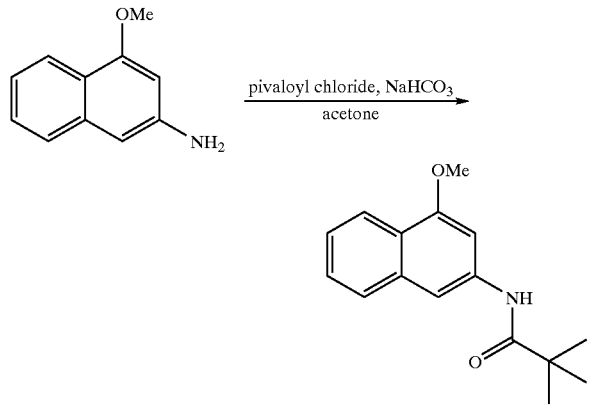

Commercially Available

A. Preparation of N-(4-methoxynaphthalen-2-yl)-2,2-dimethylpropionamide. A solution of 3-amino-1-methoxynaphthalene (5.0 g, 29 mmol) in acetone (200 mL) was treated with pivaloyl chloride (4.0 mL, 33 mmol) and the resulting suspension stirred at room temperature for 1 h. Excess sodium bicarbonate was added and the resulting mixture stirred for 1 h, filtered, and reduced in vacuo to a volume of approximately 100 mL. The mixture was diluted with water and the resulting precipitate collected via vacuum filtration. The solid was washed with water and dried under vacuum for 60° C. to provide the title compound in quantitative yield: mp 169–170° C. $^1$H NMR (CDCl$_3$) δ8.14 (d, J=7.7 Hz, 1H), 7.67 (d, J=7.1 Hz, 1H), 7.50 (s, 1H), 7.48 (bs, 1H), 7.43 (t, J=7.0 Hz, 1H), 7.35 (t, J=7.0 Hz, 1H), 7.23 (s, 1H), 4.00 (s, 3H), 1.35 (s, 9H); MS FD+ m/e 257 (p); IR (CHCl$_3$, cm$^{-1}$) 3450, 3000, 1678, 1531. Anal. Calcd for C$_{16}$H$_{19}$NO$_2$: C, 74.68; H, 7.44; N, 5.44. Found: C, 74.76; H, 7.68; N, 5.58.

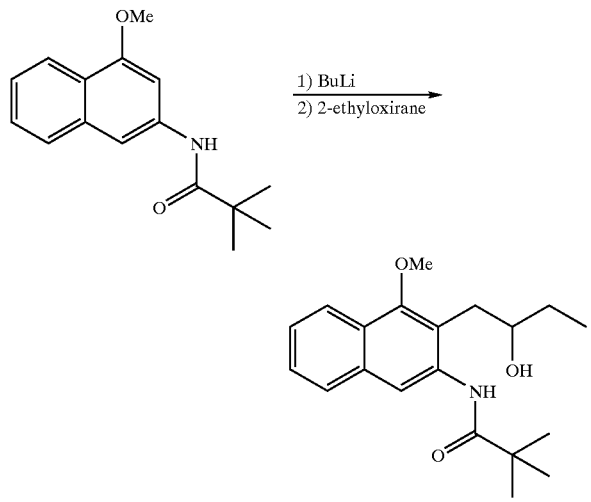

B. Preparation of N-[3-(2-hydroxybutyl)-4-methoxynaphthalen-2-yl]-2,2-dimethylpropionamide. To a solution of N-(4-methoxynaphthalen-2-yl)-2,2-dimethylpropionamide (514 mg, 2.00 mmol) in tetrahydrofuran (4 mL) cooled in an ice/acetone bath was added 2.0 M n-butyllithium in hexane (3.0 mL, 6.0 mmol) slowly via syringe. The mixture was allowed to warm to room temperature over 30 min and an additional portion of tetrahydrofuran (5 mL) was added. 2-Ethyloxirane (0.57 mL, 6.6 mmol) was added and the resulting mixture was stirred at room temperature for 40 h. The mixture was diluted with aqueous saturated ammonium chloride solution and ethyl acetate. The organic layer was washed once with saturated sodium bicarbonate solution, separated, dried (sodium sulfate), filtered, and concentrated in vacuo. Chromatography (silica gel, methylene chloride/ethyl acetate) of the residue provided 396 mg (60%) of the title compound and 140 mg (27%) of starting material: mp 173–174° C. $^1$H NMR (CDCl$_3$) δ9.19 (bs, 1H), 8.18 (s, 1H), 7.97 (m, 1H), 7.80 (m, 1H), 7.42 (m, 2H), 3.93 (m, 1H), 3.90 (s, 3H), 3.15 (dd, J=13.9, 2.0 Hz, 1H), 2.73 (dd, J=14.3, 9.4 Hz, 1H), 2.05 (bs, 1H), 1.76 (septet, J=7.5 Hz, 1H), 1.65 (septet, J=7.2 Hz, 1H), 1.36 (s, 9H), 1.07 (t, J=7.5 Hz, 3H); MS ES− m/e 328 (p−1). IR (CHCl$_3$, cm$^{-1}$) 3400 (b), 3009, 1667, 1531. Anal. Calcd for C$_{20}$H$_{27}$NO$_3$: C, 72.92; H, 8.26; N, 4.25. Found: C, 72.72; H, 8.29; N, 4.40.

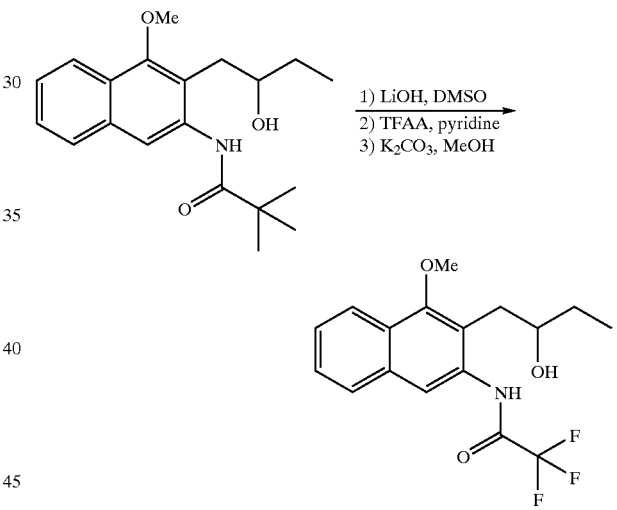

C. Preparation of 2,2,2-trifluoro-N-[3-(2-hydroxybutyl)-4-methoxynaphthalen-2-yl]acetamide. To a mixture N-[3-(2-hydroxybutyl)-4-methoxynaphthalen-2-yl]-2,2-dimethylpropionamide (3.57 g, 10.8 mmol) and lithium hydroxide (0.52 g, 22 mmol) in methyl sulfoxide (8 mL) was added 1M aqueous lithium hydroxide solution (2 mL) and a trace of methanol. The mixture was warmed to 180° C. while stirring and allowing some volatile material to distill away. After 1 h toluene (2 mL) was added and the resulting mixture stirred for 3 h and allowed to cool to room temperature. A solid mass formed that was broken up by the addition of water and ethyl acetate. The mixture was saturated with sodium chloride and the layers separated. The aqueous layer was extracted with an additional portion of ethyl acetate. The combined ethyl acetate extracts were washed once with water, dried (magnesium sulfate), filtered, and concentrated in vacuo. The residue was dissolved in methylene chloride (20 mL) and treated with pyridine (2.6 mL, 32 mmol) and trifluoroacetic anhydride (3.1 mL, 22 mmol). The mixture was stirred for 20 h and partitioned between ether and 10% aqueous citric acid. The aqueous layer was washed with an additional portion of ether. The combined ether extracts were washed once with saturated sodium bicarbonate solution, dried (magnesium sulfate), filtered, and concentrated in vacuo. The residue was dissolved in methanol and an excess of potassium carbonate was added. The mixture was stirred 30 min and partitioned between ether and water. The organic layer was separated, dried (magnesium sulfate), filtered, and concentrated in vacuo to reveal a brown oil which crystallized on standing to give 3.28 g (89%) of the title compound: mp 120–123° C. $^1$H NMR (CDCl$_3$) δ10.63 (bs, 1H), 8.19 (s, 1H), 8.01 (m, 1H), 7.82 (m, 1H), 7.48 (m, 2H), 3.95 (m, 1H), 3.90 (s, 3H), 3.22 (dd, J=14.3, 2.2 Hz, 1H), 2.77 (dd, J=14.3, 8.8 Hz, 1H), 2.23 (bs, 1H), 1.76 (septet, J=7.0 Hz, 1H), 1.58 (septet, J=7.0 Hz, 1H), 1.04 (t, J=7.3 Hz, 3H); MS ES– m/e 341 (p). IR (CHCl$_3$, cm$^{-1}$) 3465 (b), 1701, 1576, 1182. Anal. Calcd for C$_{17}$H$_{18}$F$_3$NO$_3$: C, 59.82; H, 5.32; N, 4.10. Found: C, 59.64; H, 5.13; N, 4.02.

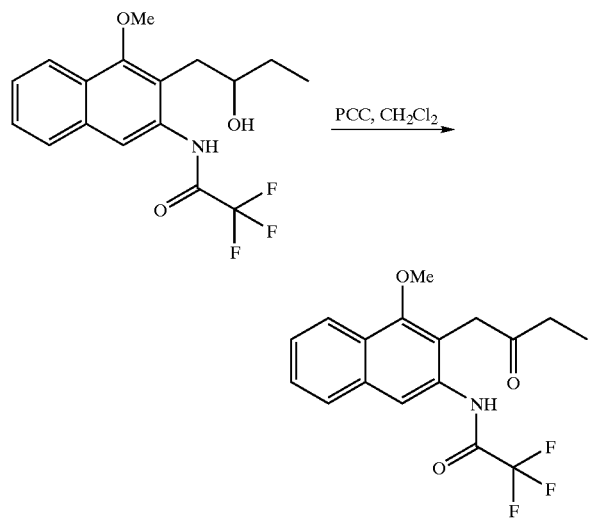

D. Preparation of 2,2,2-trifluoro-N-[4-methoxy-3-(2-oxobutyl)-naphthalen-2-yl]acetamide. To a solution of 2,2,2-trifluoro-N-[3-(2-hydroxybutyl)-4-methoxynaphthalen-2-yl]acetamide (6.24 g, 18.3 mmol) in methylene chloride (100 mL) was added pyridinium chlorochromate (6.20 g, 28.8 mmol) and the resulting mixture stirred at room temperature for 24 h. Silica gel (25 g) was added and the resulting suspension stirred for 1 h. The mixture was filtered through a pad of silica gel that was washed thoroughly with methylene chloride. The filtrate was concentrated in vacuo and the residue dissolved in a minimum of methylene chloride. This solution was diluted with hexane and the resulting precipitate collected via vacuum filtration. Cooling of the filtrate provided additional material to provide a total of 4.03 g (65%) of the title compound as yellow needles: mp 130–131° C. $^1$H NMR (CDCl$_3$) δ10.08 (bs, 1H), 8.19 (s, 1H), 8.01 (m, 1H), 7.83 (m, 1H), 7.50 (m, 2H), 3.96 (s, 2H), 3.93 (s, 3H), 2.78 (q, J=7.3 Hz, 2H), 1.07 (t, J=7.3 Hz, 3H); MS ES– m/e 338 (p–1). IR (KBr, cm$^{-1}$) 3268, 1706, 1166. Anal. Calcd for C$_{17}$H$_{16}$F$_3$NO$_3$: C, 60.18; H, 4.75; N, 4.13. Found: C, 59.92; H, 4.48; N, 4.05.

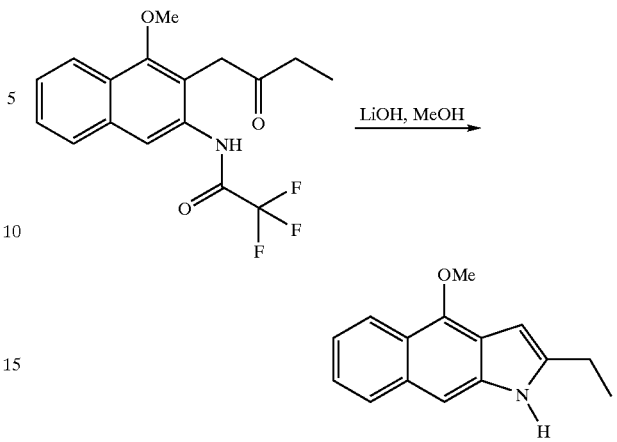

E. Preparation of 2-ethyl-4-methoxy-1H-benz[f]indole. A solution of 2,2,2-trifluoro-N-[4-methoxy-3-(2-oxobutyl)-naphthalen-2-yl]acetamide (173 mg, 0.510 mmol) in methanol (3 mL) was treated with 1 M aqueous lithium hydroxide solution (1 mL) and heated at 95° C. for 4 h and 60° C. for 18 h. The mixture was cooled to room temperature and diluted with ether. The ether layer was washed once with water and the aqueous layer separated and extracted with a fresh portion of ether. The combined ether extracts were washed once with water, dried (sodium sulfate), filtered and concentrated in vacuo. Chromatography (silica gel, methylene chloride/hexane) of the residue provided 94 mg (82%) of the title compound as an oil. $^1$H NMR (CDCl$_3$) δ8.25 (d, J=7.3 Hz, 1H), 7.82 (d, J=7.3 Hz, 1H), 7.77 (bs, 1H), 7.43 (s, 1H), 7.31 (m, 2H), 6.47 (s, 1H), 4.20 (s, 3H), 2.83 (q, J=7.7 Hz, 2H), 1.39 (t, J=7.3 Hz, 3H); MS ES– m/e 226 (p+1). IR (CHCl$_3$, cm$^{-1}$) 3472, 3009, 1418, 1314. Anal. Calcd for C$_{15}$H$_{15}$NO: C, 79.97; H, 6.71; N, 6.22. Found: C, 79.84; H, 6.82; N, 6.12.

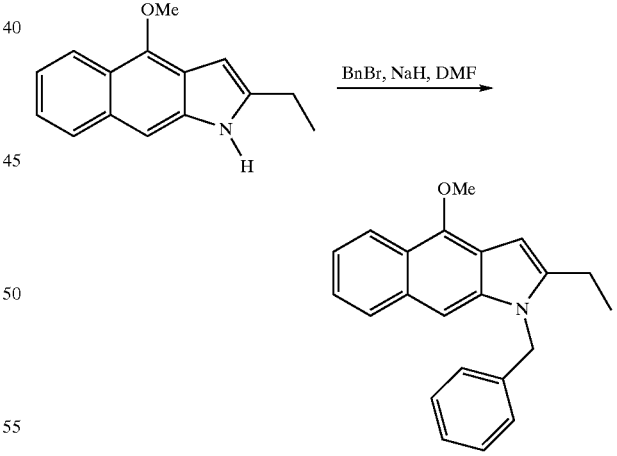

F. Preparation of 1-benzyl-2-ethyl-4-methoxy-1H-benz[f] indole. To a solution of 2-ethyl-4-methoxy-1H-benz[f] indole (548 mg, 2.43 mmol) in N,N-dimethylformamide (5 mL) was added benzyl bromide (0.64 mL, 5.8 mmol) followed by a 60% suspension of sodium hydride in mineral oil (290 mg, 7.3 mmol). After stirring for 1 h at room temperature, the mixture was diluted with water and extracted twice with ethyl acetate. The combined organic layers were washed three times with water, dried (magnesium sulfate), filtered, and concentrated in vacuo.

Chromatography (silica gel, methylene chloride/hexanes) of the residue provided 635 mg of the title compound. MS ES+ m/e 316 (p+1)

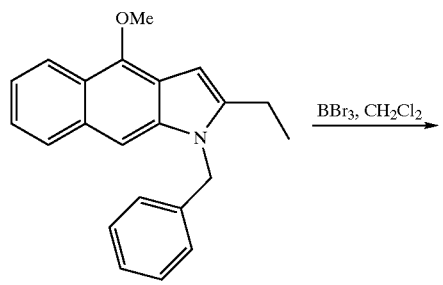

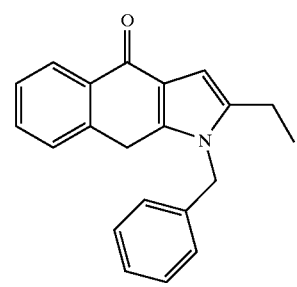

G. Preparation of 1-benzyl-2-ethyl-1,9-dihydrobenzo[f]indol-4-one. To a solution of 1-benzyl-2-ethyl-4-methoxy-1H-benz[f]indole (698 mg, 2.21 mmol) in methylene chloride (5 mL) was cooled to −10° C. and treated with boron tribromide (0.47 mL, 5.0 mmol). The mixture was warmed to 10° C. over 2.5 h then diluted with methanol. The mixture was diluted with methylene chloride and the resulting solution washed once with saturated sodium bicarbonate solution. The aqueous layer was extracted with a fresh portion of methylene chloride. The combined organic layers were washed once with water, dried (sodium sulfate), filtered, and concentrated in vacuo. Chromatography (silica gel, hexane/methylene chloride to acetone/methylene chloride) provided 310 mg (46%) of the title compound. $^1$H NMR (CDCl$_3$) δ8.38 (d, J=7.3 Hz, 1H), 7.44 (m, 2H), 7.30 (m, 4 H), 6.94 (d, J=7.0 Hz, 2H), 6.66 (S, 1H), 5.17 (s, 2H), 3.95 (s, 2H), 2.52 (q, J=7.3 Hz, 2H), 1.26 (t, J=7.3 Hz, 3H); MS ES+ m/e 302 (p+1). IR (KBr, cm$^{-1}$) 2962, 1618, 1290. Anal. Calcd for C$_{21}$H$_{19}$NO: C, 83.69; H, 6.35; N, 4.65. Found: C, 82.70; H, 6.40; N, 4.78.

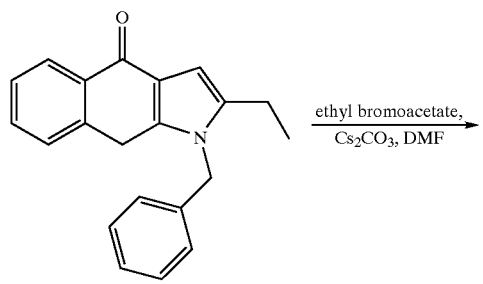

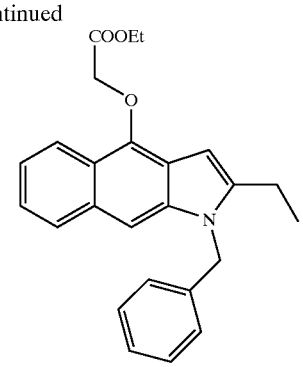

H. Preparation of (1-benzyl-2-ethyl-1H-benzo[f]indol-4-yloxy)acetic acid ethyl ester. A mixture of 1-benzyl-2-ethyl-1,9-dihydrobenzo[f]indol-4-one (301 mg, 1.00 mmol), cesium carbonate (325 mg, 1.00 mmol), and ethyl bromoacetate (0.17 mL, 15 mmol) in N,N-dimethylformamide (2 mL) was stirred at room temperature for 20 h. The mixture was diluted with ether and the resulting solution washed twice with water. The organic layer was separated, dried (magnesium sulfate), filtered, and concentrated in vacuo. Chromatography (silica gel, hexane/methylene chloride to acetone/methylene chloride) of the residue provided 168 mg (48%) of the title compound. $^1$H NMR (CDCl$_3$) δ8.38 (d, J=8.8 Hz, 1H), 7.78 (d, J=9.5 Hz, 1H), 7.37 (s, 1H), 7.31 (m, 2H), 7.24 (m, 3H), 6.98 (d, J=8.1 Hz, 2H), 6.52 (s, 1H), 5.37 (s, 2H), 4.99 (s, 2H), 4.33 (q, J=7.0 Hz, 2H), 2.74 (q, J=7.3 Hz, 2H), 1.36 (t, J=7.3 Hz, 3H), 1.33 (t, J=7.0 Hz, 3H); MS ES+ m/e 388 (p+1).

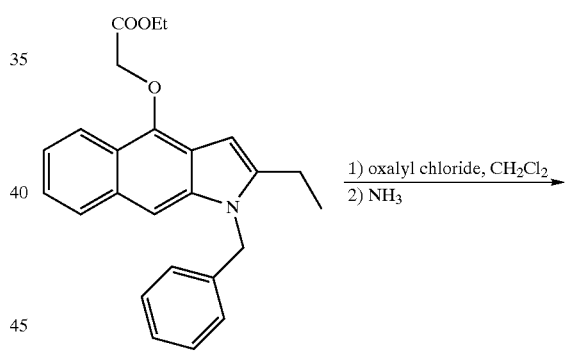

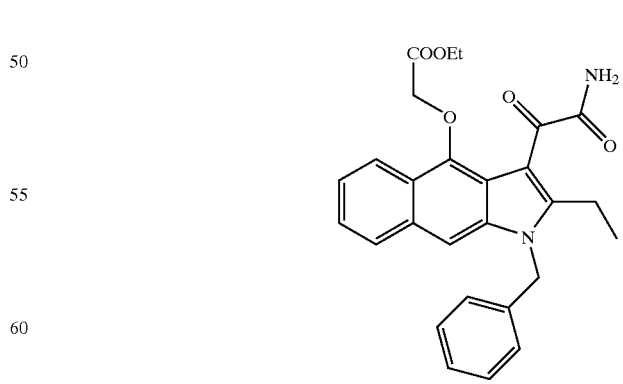

I. Preparation of 2-[[3-(2-amino-1,2-dioxoethyl)-1-benzyl-2-ethyl-1H-benz[f]indol-4-yl]oxy]acetic acid ethyl ester. A solution of (1-benzyl-2-ethyl-1H-benzo[f]indol-4-yloxy) acetic acid ethyl ester (168 mg, 0.434 mmol) in methylene chloride (10 mL) was cooled to −55° C. and treated with oxalyl chloride (1.0 mL, 11 mmol). The mixture was stirred for 2 h, warmed to −10° C., and concentrated in vacuo. The residue was dissolved in methylene chloride (10 mL) and treated with an excess of a solution of ammonia in dioxane. The mixture was stirred for 30 min and concentrated in vacuo. The residue was dissolved in methylene chloride which was washed once with water, dried (sodium sulfate), filtered, and concentrated in vacuo. HPLC purification of the residue provided 74 mg (37%) of the title compound as a yellow powder. ¹H NMR (CDCl₃) δ8.17 (d, J=7.7 Hz, 1H), 7.78 (d, J=6.8 Hz, 1H), 7.42 (s, 1H), 7.34 (m, 2H), 7.28 (m, 3H), 7.08 (d, J=8.1 Hz, 2H), 6.84 (bs, 1H), 5.49 (bs, 1H), 5.44 (s, 2H), 4.76 (s, 2H), 4.18 (q, J=6.9 Hz, 2H), 3.05 (q, J=7.3 Hz, 2H), 1.26 (t, J=7.7 Hz, 3H), 1.20 (t, J=7.3 Hz, 3H); MS ES+ m/e 459 (p+1).

EXAMPLE 2

Preparation of 2-[[3-(2-amino-1,2-dioxoethyl)-1-benzyl-2-ethyl-1H-benz[f]indol-4-yl]oxy]acetic acid benzyl ester.

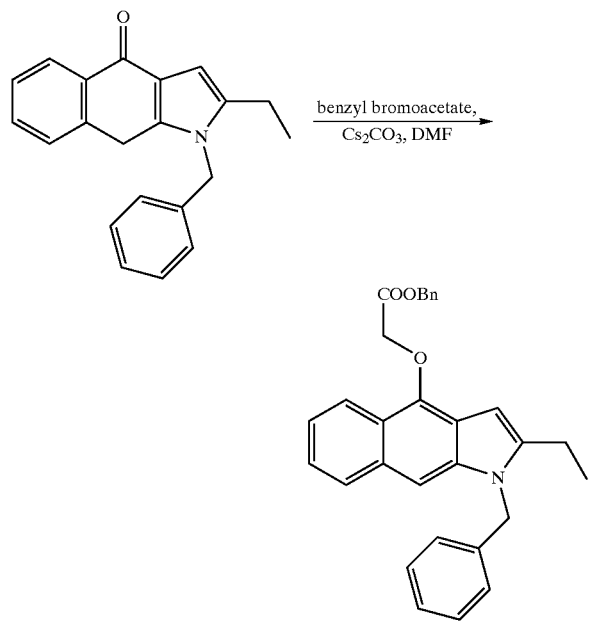

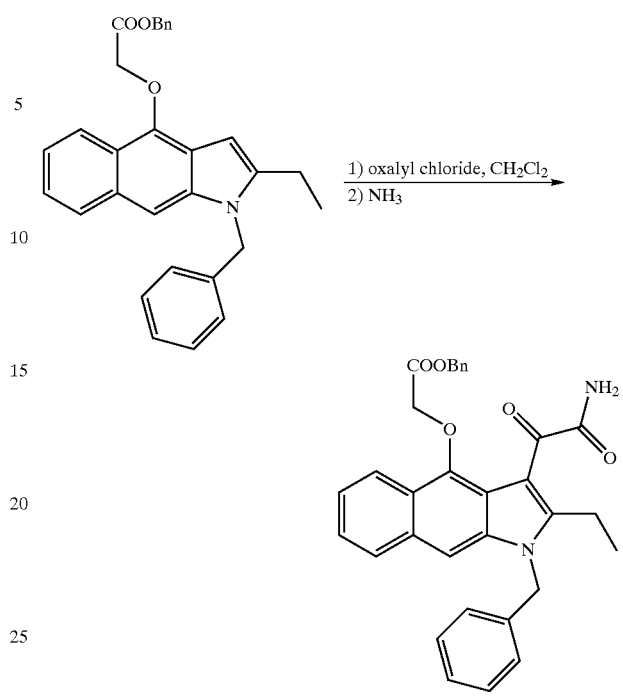

A. Preparation of (1-benzyl-2-ethyl-1H-benzo[f]indol-4-yloxy)acetic acid benzyl ester. A mixture of 1-benzyl-2-ethyl-1,9-dihydrobenzo[f]indol-4-one (200 mg, 0.67 mmol), cesium carbonate (436 mg, 1.39 mmol), and ethyl bromoacetate (0.21 mL, 1.34 mmol) in N,N-dimethylformamide (5 mL) was stirred at room temperature for 20 h. The mixture was diluted with water and the resulting solution extracted three times with ethyl acetate. The combined ethyl acetate extracts were washed three times with water, filtered through a plug of silica gel, and concentrated in vacuo. Chromatography (hexane/methylene chloride) of the residue provided 120 mg (40%) of the title compound as a yellow film.

¹H NMR (CDCl₃) δ8.38 (m, 1H), 7.77 (m, 1H), 7.37 (m, 6H), 7.30 (m, 2H), 7.23 (m, 3H), 6.97 (d, J=6.6 Hz, 2H), 6.49 (bs, 1H), 5.36 (s, 2H), 5.29 (s, 2H), 5.05 (s, 2H), 2.70 (q, J=7.4 Hz, 2H), 1.33 (t, J=7.3 Hz, 3H); MS ES+ m/e 450 (p+1).

B. Preparation of 2-[[3-(2-amino-1,2-dioxoethyl)-1-benzyl-2-ethyl-1H-benz[f]indol-4-yl]oxy]acetic acid benzyl ester. A solution of (1-benzyl-2-ethyl-1H-benzo[f]indol-4-yloxy) acetic acid benzyl ester (110 mg, 0.24 mmol) in methylene chloride (2 mL) was cooled to in an ice/methanol bath and treated with oxalyl chloride (0.20 mL, 2.2 mmol). The mixture was stirred for 1.5 h while warming to −10° C., then concentrated in vacuo. The residue was dissolved in methylene chloride (5 mL) and treated with an excess of a solution of ammonia in dioxane. The mixture was stirred for 15 min and concentrated in vacuo. Chromatography (silica gel, methylene chloride/ether) of the residue provided 64 mg (51%) of the title compound as a brown foam. ¹H NMR (CDCl₃) δ8.15 (m, 1H), 7.78 (m, 1H), 7.41 (s, 1H), 7.33 (m, 7H), 7.29 (m, 3H), 7.08 (d, J=8.0 Hz, 2H), 6.45 (bs, 1H), 5.43 (s, 2H), 5.30 (bs, 1H), 5.17 (s, 2H), 4.80 (s, 2H), 3.04 (q, J=7.7 Hz, 2H), 1.25 (t, J=7.7 Hz, 3H); MS ES+ m/e 521 (p+1); IR (KBr, cm⁻¹) 3458, 1757, 1695, 1640.

EXAMPLE 3

Preparation of 2-[[3-(2-amino-1,2-dioxoethyl)-1-benzyl-2-ethyl-1H-benz[f]indol-4-yl]oxy]acetic acid.

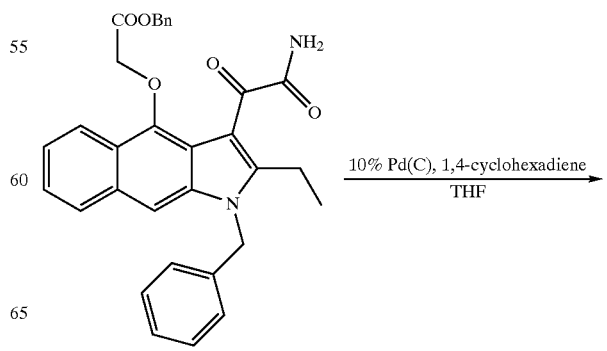

-continued

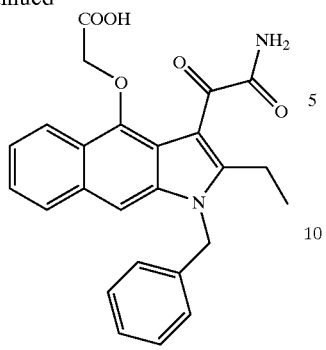

Preparation of 2-[[3-(2-amino-1,2-dioxoethyl)-1-benzyl-2-ethyl-1H-benz[f]indol-4-yl]oxy]acetic acid. A mixture of 2-[[3-(2-amino-1,2-dioxoethyl)-1-benzyl-2-ethyl-1H-benz[f]indol-4-yl]oxy]acetic acid benzyl ester (29 mg, 0.056 mmol), 10% palladium-on-carbon (30 mg), and 1,4-cyclohexadiene (1 mL) in tetrahydrofuran (1 mL) was warmed to 50° C. with stirring for 3 h. The mixture was filtered and the resulting solution concentrated in vacuo. The filtered solids were washed with methanol and the resulting solution concentrated in vacuo. Both residues were dissolved methylene chloride and diluted with hexane. The resulting precipitate was collected via vacuum filtration to provide 8.8 mg (37%) of the title compound as a solid: mp 243–253° C. (dec). $^1$H NMR (DMSO-$d_6$) δ8.26 (m, 1H), 8.11 (bs, 1H), 7.89 (m, 1H), 7.75 (s, 1H), 7.53 (s, 1H), 7.34 (m, 2H), 7.30 (m, 2H), 7.22 (t, J=7.0 Hz, 1H), 7.07 (d, J=7.3 Hz, 2H), 5.60 (s, 2H), 4.47 (s, 2H), 2.97 (q, J=7.7 Hz, 2H), 1.10 (t, J=7.3 Hz, 3H); TOF MS ES+ exact mass calculated for $C_{25}H_{23}N_2O_5$: m/z=431.1607 (p+1). Found: 431.1605.

We claim:

1. A benz[f]indole compound of formula (I), or a pharmaceutically acceptable salt, solvate or prodrug thereof:

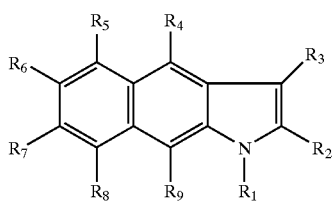
(I)

wherein;

$R_1$ is selected from group (a) or (c) wherein;
(a) is $C_2$–$C_{20}$ alkyl, $C_2$–$C_{20}$ haloalkyl, $C_2$–$C_{20}$ alkenyl, $C_2$–$C_{20}$ alkynyl or carbocyclic radical, or
(c) is the group -(L)-$R_{80}$; where, -(L)- is a divalent linking group of 1 to 12 atoms selected from carbon and hydrogen; and where $R_{80}$ is a group selected from (a);

$R_2$ is hydrogen, ($C_1$–$C_4$) alkyl, ($C_2$–$C_4$)alkenyl, —O—($C_1$–$C_3$ alkyl), —S—($C_1$–$C_3$ alkyl), ($C_3$–$C_4$) cycloalkyl, —$CF_3$, halo, —$NO_2$, —CN, or —$SO_3$;

$R_3$ is -(L$_3$)-Z, where -(L$_3$)- is a bond
and Z is selected from an oxime amide or oxime thioamide group represented by the formulae,

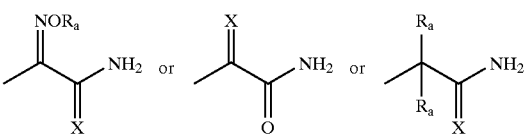

wherein X is oxygen or sulfur, $R_a$ is independently selected from hydrogen, $C_1$–$C_8$ alkyl, aryl, $C_1$–$C_8$ alkaryl, $C_1$–$C_8$ alkoxy, aralkyl and —CN;

$R_4$ is the group, hydrogen, $CONH_2$, $CONHR^{4b}$ or -(La)-(COOH) wherein -(L$_a$)-, is $OCH_2$;

or the group -(L$_h$)-(N-hydroxyfunctional amide group); wherein -(L$_h$)-, is $OCH_2$; and wherein the N-hydroxyfunctional amide group is represented by the formula:

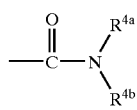

wherein $R^{4a}$ is selected from the group consisting of OH, ($C_1$–$C_6$)alkoxy, and aryloxy; and wherein $R^{4b}$ is hydrogen or an organic substituent selected from the group consisting of ($C_1$–$C_8$)alkyl, aryl, ($C_7$–$C_{14}$)aralkyl, ($C_7$–$C_{14}$)alkaryl, ($C_3$–$C_8$) cycloalkyl and ($C_1$–$C_8$)alkoxyalkyl;

$R_5$ is selected from hydrogen, ($C_1$–$C_8$)alkyl, ($C_2$–$C_8$) alkenyl, ($C_2$–$C_8$) alkynyl, ($C_7$–$C_{12}$)aralkyl, ($C_7$–$C_{12}$) alkaryl, ($C_3$–$C_8$)cycloalkyl, ($C_3$–$C_8$)cycloalkenyl, phenyl, toluyl, xylenyl, biphenyl, ($C_1$–$C_8$)alkoxy, ($C_2$–$C_8$)alkenyloxy, ($C_2$–$C_8$)alkynyloxy, ($C_2$–$C_{12}$) alkoxyalkyl, ($C_2$–$C_{12}$)alkoxyalkyloxy and ($C_1$–$C_{12}$) alkylamino; and wherein $R_6$, $R_7$, $R_8$, and $R_9$ are independently selected from ($C_1$–$C_8$)alkyl, ($C_2$–$C_8$)alkenyl, ($C_2$–$C_8$) alkynyl, ($C_7$–$C_{12}$)aralkyl, ($C_7$–$C_{12}$)alkaryl, ($C_3$–$C_8$)cycloalkyl, ($C_3$–$C_8$)cycloalkenyl, phenyl, toluyl, xylenyl, biphenyl, ($C_1$–$C_8$)alkoxy, ($C_2$–$C_8$)alkenyloxy, ($C_2$–$C_8$) alkynyloxy, ($C_2$–$C_{12}$)alkoxyalkyl and ($C_1$–$C_{12}$) alkylamino.

2. The compound of claim 1 wherein $R_2$, is hydrogen, ($C_1$–$C_4$)alkyl, ($C_2$–$C_4$)alkenyl, —O—($C_1$–$C_3$ alkyl), or ($C_3$–$C_4$)cycloalkyl.

3. The compound of claim 1 wherein for $R_3$, Z is the group represented by the formula;

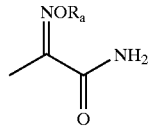

and the linking group, -(L$_3$)-, $R_a$ is hydrogen, methyl, ethyl, propyl, isopropyl, phenyl or benzyl.

4. The compound of claim 1 wherein for $R_3$, Z is the group represented by the formula;

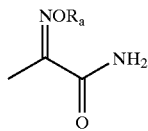

and the linking group -($L_3$)- is a bond; and $R_a$ is hydrogen.

5. The compound of claim 1 wherein for $R_3$, Z is the group represented by the formula;

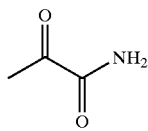

and the linking group -($L_3$)- is a bond.

6. The compound of claim 1 wherein for $R_3$, Z is the group represented by the formula;

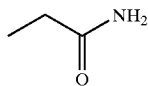

and the linking group -($L_3$)- is a bond.

7. The compound of claim 1 wherein $R_4$ is the group, -($L_h$)-(N-hydroxyfunctional amide group) and wherein the -($L_h$)- is $OCH_2$, and the (N-hydroxyfunctional amide group) is:

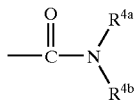

and $R^{4a}$ is independently selected from the group consisting of hydrogen, —OH, ($C_1$–$C_6$)alkoxy, and aryloxy; and wherein $R^{4b}$ is independently selected from the group consisting of H, ($C_1$–$C_6$)alkyl, ($C_7$–$C_{14}$)aralkyl, and aryl.

8. The compound of claim 1 wherein $R_4$ is the group -($L_a$)-(COOH).

9. A compound selected from the group consisting of:
2-[[3-(2-amino-1,2-dioxoethyl)-1-benzyl-2-ethyl-1H-benz[f]indol-4-yl]oxy]acetic acid ethyl ester;
2-[[3-(2-amino-1,2-dioxoethyl)-1-benzyl-2-ethyl-1H-benz[f]indol-4-yl]oxy]acetic acid benzyl ester; and
2-[[3-(2-amino-1,2-dioxoethyl)-1-benzyl-2-ethyl-1H-benz[f]indol-4-yl]oxy]acetic acid, or a pharmaceutically acceptable salt, solvate or prodrug thereof.

10. A benz[f]indole compound represented by the formulae (C1), (C2), (C3), (C4), (C5), (C6), (C7), (C8), (C9), or (C10):

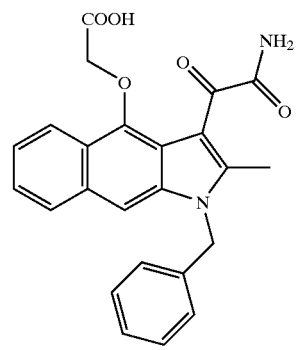
(C1)

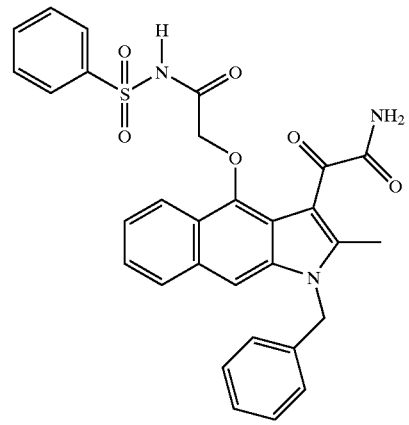
(C2)

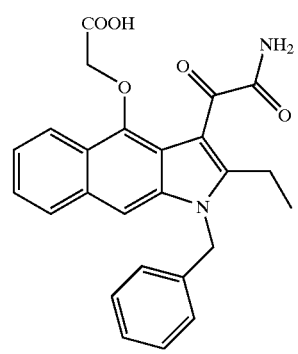
(C3)

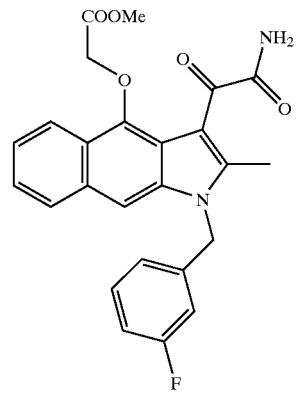
(C4)

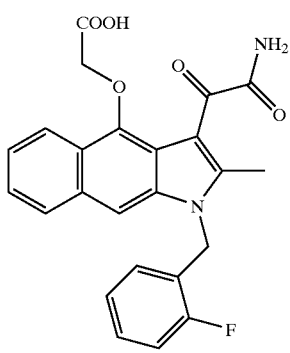

(C5)

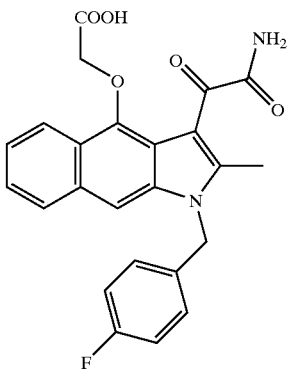

(C8)

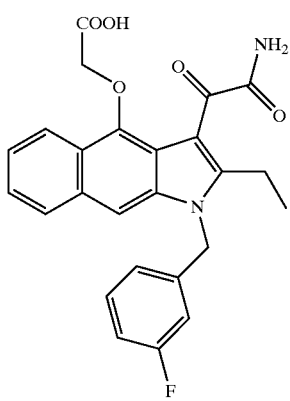

(C6)

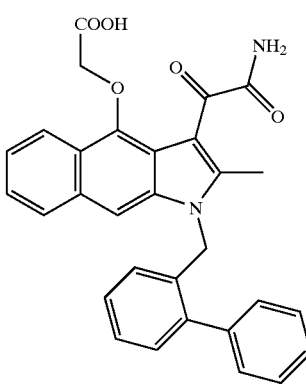

(C9)

, or

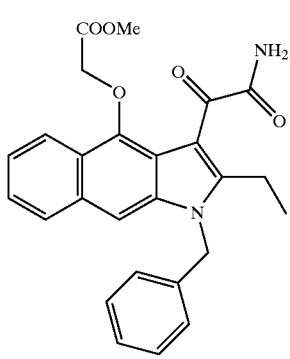

(C7)

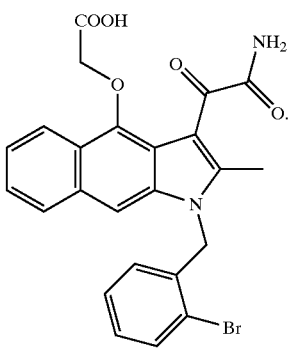

(C10)

11. A pharmaceutical composition comprising a benz[f]indole compound of claim 1 together with a pharmaceutically acceptable carrier or diluent.

12. A method of treating a mammal to alleviate the pathological effects of Inflammatory Diseases; wherein the method comprises administering to said mammal a therapeutically effective amount of a benz[f]indole compound according to claim 1.

13. A pharmaceutical composition containing a therapeutically effective amount of a compound of claim 1 useful for inhibiting sPLA$_2$ mediated release of fatty acid.

* * * * *